United States Patent
Stahmann et al.

(10) Patent No.: US 7,572,225 B2
(45) Date of Patent: Aug. 11, 2009

(54) SLEEP LOGBOOK

(75) Inventors: Jeffrey E. Stahmann, Ramsey, MN (US); Jesse W. Hartley, Lino Lakes, MN (US); Quan Ni, Shoreview, MN (US); Kent Lee, Eridley, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 868 days.

(21) Appl. No.: 10/920,569

(22) Filed: Aug. 17, 2004

(65) Prior Publication Data

US 2005/0085738 A1    Apr. 21, 2005

Related U.S. Application Data

(60) Provisional application No. 60/504,229, filed on Sep. 18, 2003.

(51) Int. Cl.
  *A61B 5/08* (2006.01)
  *A61B 5/02* (2006.01)
  *A61B 5/00* (2006.01)
  *A61B 5/103* (2006.01)

(52) U.S. Cl. .................. 600/484; 600/483; 600/529; 600/300; 600/595

(58) Field of Classification Search ......... 600/529–543, 600/481, 483, 484, 300, 595; 607/2–32
See application file for complete search history.

(56) References Cited

U.S. PATENT DOCUMENTS

| | | | |
|---|---|---|---|
| 4,365,636 A | 12/1982 | Barker | |
| 4,562,841 A | 1/1986 | Brockway et al. | |
| 4,702,253 A | 10/1987 | Nappholz et al. | |
| 4,813,427 A | 3/1989 | Schlaefke et al. | |
| 4,827,935 A | 5/1989 | Geddes et al. | |
| 4,830,008 A | 5/1989 | Meer | |
| 4,928,688 A | 5/1990 | Mower | |
| 5,036,849 A | 8/1991 | Hauck et al. | |
| 5,105,354 A | 4/1992 | Nishimura | |
| 5,123,425 A | 6/1992 | Shannon, Jr. et al. | |
| 5,146,918 A | 9/1992 | Kallok et al. | |
| 5,178,156 A | 1/1993 | Takishima et al. | |

(Continued)

FOREIGN PATENT DOCUMENTS

EP    0 940 155 A    9/1999

(Continued)

OTHER PUBLICATIONS

Balaban et al., *Feasibility of Screening for Sleep Apnea Using Pacemaker Impedance Sensor*, NASPE (2001).

(Continued)

*Primary Examiner*—Charles A Marmor, II
*Assistant Examiner*—Navin Natnithithadha
(74) *Attorney, Agent, or Firm*—Hollingsworth & Funk, LLC

(57) ABSTRACT

An approach to collecting and organizing information associated with events affecting sleep is presented. The sleep logbook system may acquire information associated with the sleep during periods of sleep and/or during periods of wakefulness. The information is organized as a sleep logbook entry. The user can access the sleep information by operating a user interface. The information may be presented in textual or graphical form.

40 Claims, 28 Drawing Sheets

U.S. PATENT DOCUMENTS

| | | |
|---|---|---|
| 5,187,657 A | 2/1993 | Forbes |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,284,136 A | 2/1994 | Hauck et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,466,245 A | 11/1995 | Spinelli et al. |
| 5,483,969 A | 1/1996 | Testerman et al. |
| 5,485,851 A | 1/1996 | Erickson |
| 5,487,755 A | 1/1996 | Snell et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,603,732 A | 2/1997 | Dahl et al. |
| 5,645,570 A | 7/1997 | Corbucci |
| 5,738,102 A | 4/1998 | Lemelson |
| 5,814,087 A | 9/1998 | Renirie |
| 5,836,987 A | 11/1998 | Baumann et al. |
| 5,844,680 A | 12/1998 | Sperling |
| 5,855,593 A | 1/1999 | Olson et al. |
| 5,871,011 A | 2/1999 | Howell et al. |
| 5,891,023 A | 4/1999 | Lynn |
| 5,911,218 A | 6/1999 | DiMarco |
| 5,916,243 A | 6/1999 | KenKnight et al. |
| 5,944,680 A | 8/1999 | Christopherson et al. |
| 5,964,778 A | 10/1999 | Fugoso et al. |
| 5,974,340 A | 10/1999 | Kadhiresan |
| 6,021,351 A | 2/2000 | Kadhiresan et al. |
| 6,026,320 A | 2/2000 | Carlson et al. |
| 6,044,298 A | 3/2000 | Salo et al. |
| 6,045,513 A | 4/2000 | Stone et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,190,326 B1 | 2/2001 | McKinnon et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,263,244 B1 | 7/2001 | Mann et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,358,203 B2 | 3/2002 | Bardy |
| 6,363,270 B1 | 3/2002 | Colla et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,398,728 B1 | 6/2002 | Bardy |
| 6,411,848 B2 | 6/2002 | Kramer et al. |
| 6,415,183 B1 | 7/2002 | Scheiner et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,459,929 B1 | 10/2002 | Hopper et al. |
| 6,480,733 B1 | 11/2002 | Turcott |
| 6,487,443 B2 | 11/2002 | Olson et al. |
| 6,529,752 B2 * | 3/2003 | Krausman et al. ............ 600/323 |
| 6,542,775 B2 | 4/2003 | Ding et al. |
| 6,574,507 B1 | 6/2003 | Bonnet |
| 6,580,944 B1 | 6/2003 | Katz et al. |
| 6,589,188 B1 | 7/2003 | Street et al. |
| 6,597,951 B2 | 7/2003 | Kadhiresan et al. |
| 6,641,542 B2 * | 11/2003 | Cho et al. .................... 600/529 |
| 6,741,885 B1 | 5/2004 | Bornzin et al. |
| 6,773,404 B2 | 8/2004 | Poezevera et al. |
| 6,810,287 B2 | 10/2004 | Zhu et al. |
| 6,964,641 B2 | 11/2005 | Cho et al. |
| 7,089,936 B2 | 8/2006 | Madaus et al. |
| 7,207,945 B2 | 4/2007 | Bardy |
| 7,225,013 B2 | 5/2007 | Geva et al. |
| 7,252,640 B2 | 8/2007 | Ni et al. |
| 2002/0193697 A1 * | 12/2002 | Cho et al. .................... 600/529 |
| 2002/0193839 A1 | 12/2002 | Cho et al. |
| 2002/0193967 A1 | 12/2002 | Siegel |
| 2003/0023184 A1 | 1/2003 | Pitts-Crick et al. |
| 2003/0055461 A1 | 3/2003 | Girouard et al. |
| 2003/0100925 A1 | 5/2003 | Pape et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2004/0002742 A1 | 1/2004 | Florio |
| 2004/0030362 A1 | 2/2004 | Hill et al. |
| 2004/0088027 A1 | 5/2004 | Burnes et al. |
| 2004/0102814 A1 | 5/2004 | Sorensen et al. |
| 2004/0116981 A1 | 6/2004 | Mazar |
| 2004/0122487 A1 | 6/2004 | Hatlestad et al. |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2005/0043772 A1 | 2/2005 | Stahmann et al. |
| 2005/0107838 A1 * | 5/2005 | Lovett et al. .................. 607/17 |

FOREIGN PATENT DOCUMENTS

| | | |
|---|---|---|
| EP | 1 151 718 | 11/2001 |
| EP | 1 172 125 A1 | 1/2002 |
| WO | 99/04841 | 4/1999 |
| WO | WO 00/01438 A | 1/2000 |
| WO | WO 00/17615 | 3/2000 |

| | | |
|---|---|---|
| WO | 02/087696 | 11/2002 |

OTHER PUBLICATIONS

Bradley et al., *Pathophysiologic and Therapeutic Implications of Sleep Apnea in Congestive Heart Failure*, 3 J. Cardiac Failure 223-240 (1996). Abstract only.

Bradley et al., *Sleep Apnea and Heart Failure, Park I: Obstructive Sleep Apean*, 107 Circulation 1671-1678 (2003).

Garrigue et al., *Night Atrial Overdrive with DDD Pacing Results in a Significant Reduction of Sleep Apnea Episodes and QOL Improvement in Heart Failure Patients*, NASPE (2001).

Garrigue et al., *Benefit of Atrial Pacing in Sleep Apnea Syndrome*, 346 N. Engl. J. Med. 404-412 (2002). Abstract only.

Hilton et al., *Evaluation of Frequency and Time-frequency Spectral Analysis of Heart Rate Variability as a Diagnostic Marker of the Sleep Apean Syndrome*, 37 Med. Biol. Eng. Comput. 760-769 (1999). Abstract only.

Jais et al., *Night Atrial Overdrive with DDD Pacing: a New Therapy for Sleep Apnea Syndrome*, NASPE (2000).

Javaheri et al., *Sleep Apnea in 81 Ambulatory Male Patients with Stable Heart Failure: Types and Their Prevalences, Consequences, and Presentations*, 97 Circulation 2154-2159 (1998).

Olusola et al., *Nightcap: Laboratory and home-based evaluation of a portable sleep monitor*, 32 Psychophysiology, 32-98 (1995). Abstract only.

Verrier et al., *Sleep, dreams, and sudden death: the case for sleep as an autonomic stress test for the heart*, 31 Cardiovascular Research 181-211 (1996).

Verrier et al., *Sleep Related Cardiovascular Risk: New Home-Based Monitoring Technology for Improved Diagnosis and Therapy*, 2 A.N.E. 158-175 (1997).

Roche et al., *Screening of Obstructive Sleep Apnea Syndrome by Heart Rate Variability Analysis*, 100 Circulation 1411-1455 (1999).

Shahrokh, *A Mechanism of Central Sleep Apnea in Patients With Heart Failure*, 341 N. Engl. J. Med. 949-954 (1999). Abstract only.

Vanninen et al., *Cardiac Sympathovagal Balance During Sleep Apnea Episodes*, 16 Clin. Physiol. 209-216 (1996) Abstract only.

Waldemark et al., *Detection of Apnea using Short Window FFT Technique and Artificial Neural Network*, 3390 SPIE International Society for Optical Engineering 122-133 (1998).

Young et al., *The Occurrence of Sleep-Disordered Breathing Among Middle Aged Adults*, N. Engl. J. Med. 1230-1235 (1993). Abstract only.

Guidant System Guide, Vitality AVT™, Automatic Implantable Cardioverter Defibrillator Model A135, Part 1 of 2, Chapter 7, pp. 7-1 through 7-30, 2003.

* cited by examiner

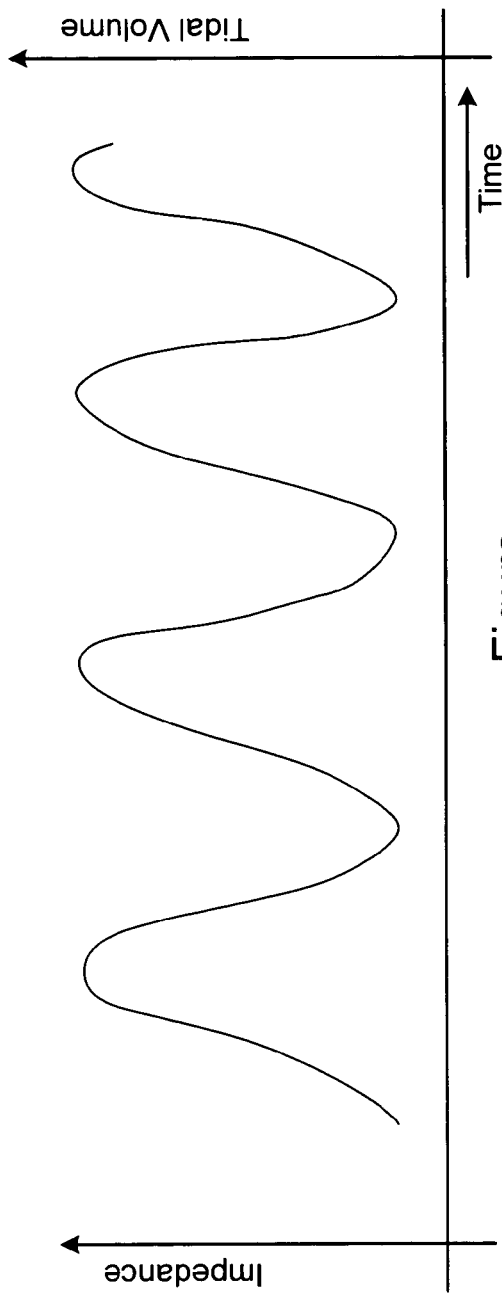
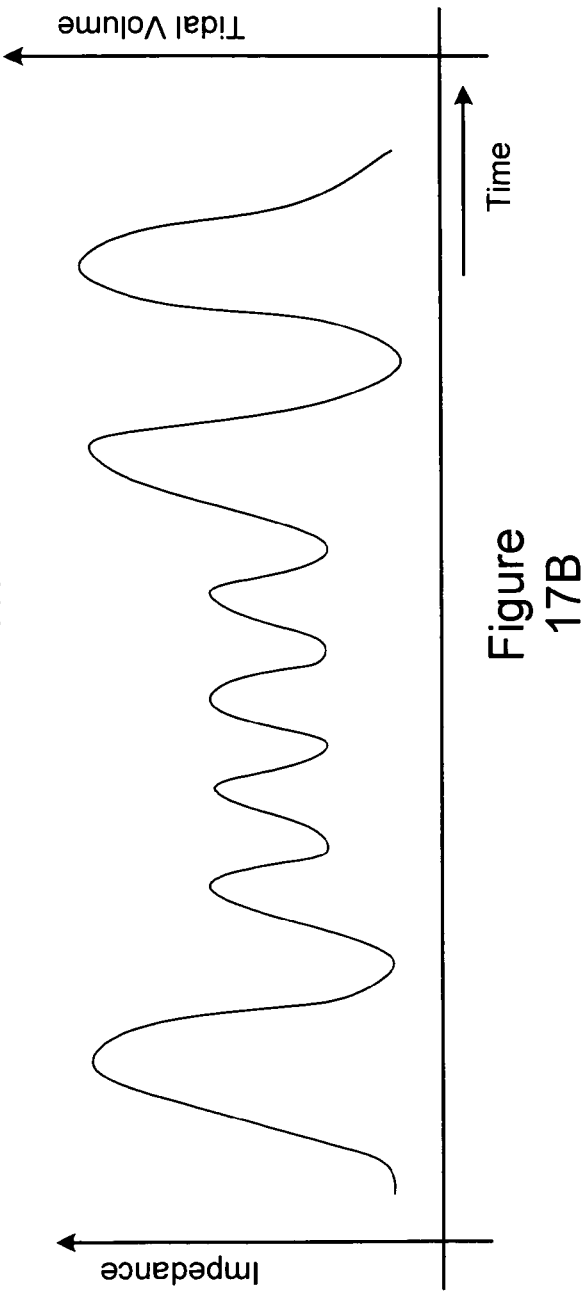
Figure 17A
Figure 17B

Trigger On                            Trigger Off

SLEEP LOGBOOK

RELATED PATENT DOCUMENTS

This application claims the benefit of Provisional Patent Application Ser. No. 60/504,229, filed on Sep. 18, 2003, to which priority is claimed pursuant to 35 U.S.C. §119(e) and which is hereby incorporated herein by reference in its entirety.

FIELD OF THE INVENTION

The present invention relates to acquiring and organizing information related to sleep and events occurring during sleep.

BACKGROUND OF THE INVENTION

Sleep is generally beneficial and restorative to a patient, exerting great influence on the quality of life. The human sleep/wake cycle generally conforms to a circadian rhythm that is regulated by a biological clock. Regular periods of sleep enable the body and mind to rejuvenate and rebuild. The body may perform various tasks during sleep, such as organizing long term memory, integrating new information, and renewing tissue and other body structures.

Normal sleep is characterized by a general decrease in metabolic rate, body temperature, blood pressure, breathing rate, heart rate, cardiac output, sympathetic nervous activity, and other physiological functions. However, studies have shown that the brain's activity does not decrease significantly during sleep. Normally a patient alternates between rapid eye movement (REM) and non-REM (NREM) sleep in approximately 90 minute cycles throughout a sleep period. A typical eight hour sleep period may be characterized in terms of a five-step sleep cycle identifiable through brain wave activity.

Non-REM sleep includes four sleep states or stages that range from light dozing to deep sleep. Throughout NREM sleep, muscle activity is still functional, breathing is low, and brain activity is minimal. Approximately 85% of the sleep cycle is spent in NREM sleep. Stage 1 NREM sleep may be considered a transition stage between wakefulness and sleep. As sleep progresses to stage 2 NREM sleep, eye movements become less frequent and brain waves increase in amplitude and decrease in frequency. As sleep becomes progressively deeper, the patient becomes more difficult to arouse. Stage 3 sleep is characterized by 20 to 40% slow brain wave (delta) sleep as detected by an electroencephalogram (EEG). Sleep stages 3 and 4 are considered to be the most restful sleep stages.

REM sleep is associated with more prevalent dreaming, rapid eye movements, muscle paralysis, and irregular breathing, body temperature, heart rate and blood pressure. Brain wave activity during REM sleep is similar to brain wave activity during a state of wakefulness. There are typically 4-6 REM periods per night, with increasing duration and intensity toward morning. While dreams can occur during either REM or NREM sleep, the nature of the dreams varies depending on the type of sleep. REM sleep dreams tend to be more vivid and emotionally intense than NREM sleep dreams. Furthermore, autonomic nervous system activity is dramatically altered when REM sleep is initiated.

Lack of sleep and/or decreased sleep quality may be have a number of causal factors including, e.g., nerve or muscle disorders, respiratory disturbances, and emotional conditions, such as depression and anxiety. Chronic, long-term sleep-related disorders e.g., chronic insomnia, sleep-disordered breathing, and sleep movement disorders, including restless leg syndrome (RLS), periodic limb movement disorder (PLMD) and bruxism, may significantly affect a patient's sleep quality and quality of life.

Movement disorders such as restless leg syndrome (RLS), and a related condition, denoted periodic limb movement disorder (PLMD), are emerging as one of the more common sleep disorders, especially among older patients. Restless leg syndrome is a disorder causing unpleasant crawling, prickling, or tingling sensations in the legs and feet and an urge to move them for relief. RLS leads to constant leg movement during the day and insomnia or fragmented sleep at night. Severe RLS is most common in elderly people, although symptoms may develop at any age. In some cases, it may be linked to other conditions such as anemia, pregnancy, or diabetes.

Many RLS patients also have periodic limb movement disorder (PLMD), a disorder that causes repetitive jerking movements of the limbs, especially the legs. These movements occur approximately every 20 to 40 seconds and cause repeated arousals and severely fragmented sleep.

A significant percentage of patients between 30 and 60 years experience some symptoms of disordered breathing, primarily during periods of sleep. Sleep disordered breathing is associated with excessive daytime sleepiness, systemic hypertension, increased risk of stroke, angina and myocardial infarction. Disturbed respiration can be particularly serious for patients concurrently suffering from cardiovascular deficiencies. Disordered breathing is particularly prevalent among congestive heart failure patients, and may contribute to the progression of heart failure.

Sleep apnea is a fairly common breathing disorder characterized by periods of interrupted breathing experienced during sleep. Sleep apnea is typically classified based on its etiology. One type of sleep apnea, denoted obstructive sleep apnea, occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and occasionally for a minute or longer.

In addition to apnea, other types of disordered respiration have been identified, including, for example, hypopnea (shallow breathing), dyspnea (labored breathing), hyperpnea (deep breathing), and tachypnea (rapid breathing). Combinations of the disordered respiratory events described above have also been observed. For example, Cheyne-Stokes respiration (CSR) is associated with rhythmic increases and decreases in tidal volume caused by alternating periods of hyperpnea followed by apnea and/or hypopnea. The breathing interruptions of CSR may be associated with central apnea, or may be obstructive in nature. CSR is frequently observed in patients with congestive heart failure (CHF) and is associated with an increased risk of accelerated CHF progression.

An adequate duration and quality of sleep is required to maintain physiological homeostasis. Untreated, sleep disturbances may have a number of adverse health and quality of life consequences ranging from high blood pressure and other cardiovascular disorders to cognitive impairment, headaches, degradation of social and work-related activities, and increased risk of automobile and other accidents.

SUMMARY OF THE INVENTION

Embodiments of the invention are directed to methods and systems for organizing information related to sleep and/or events occurring during sleep. One embodiment of the invention involves an automated method for collecting and organizing information associated with sleep. The method includes detecting sleep and acquiring information associated with sleep. The acquired information is organized as a sleep logbook. At least one of detecting sleep, acquiring the information associated with sleep, and organizing the acquired information is performed at least in part implantably.

Another embodiment involves a method for organizing sleep-related information. The method includes acquiring information associated with one or more sleep periods. The information associated with the one or more sleep periods is organized as a sleep logbook. A user interface is provided for accessing the sleep logbook.

In another embodiment of the invention, a sleep logbook system provides organized sleep information. The sleep logbook includes a sleep detector configured to detect sleep. A data acquisition unit acquires sleep information related to sleep. A processor is coupled to the sleep detector and the data acquisition unit. The processor organizes the acquired sleep information as a sleep logbook entry. At least one of the sleep detector, the data acquisition unit, and the processor includes an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 17A-B are graphs of respiration patterns derived from transthoracic impedance measurements that may be utilized in accordance with embodiments of the invention;

Figure 1:
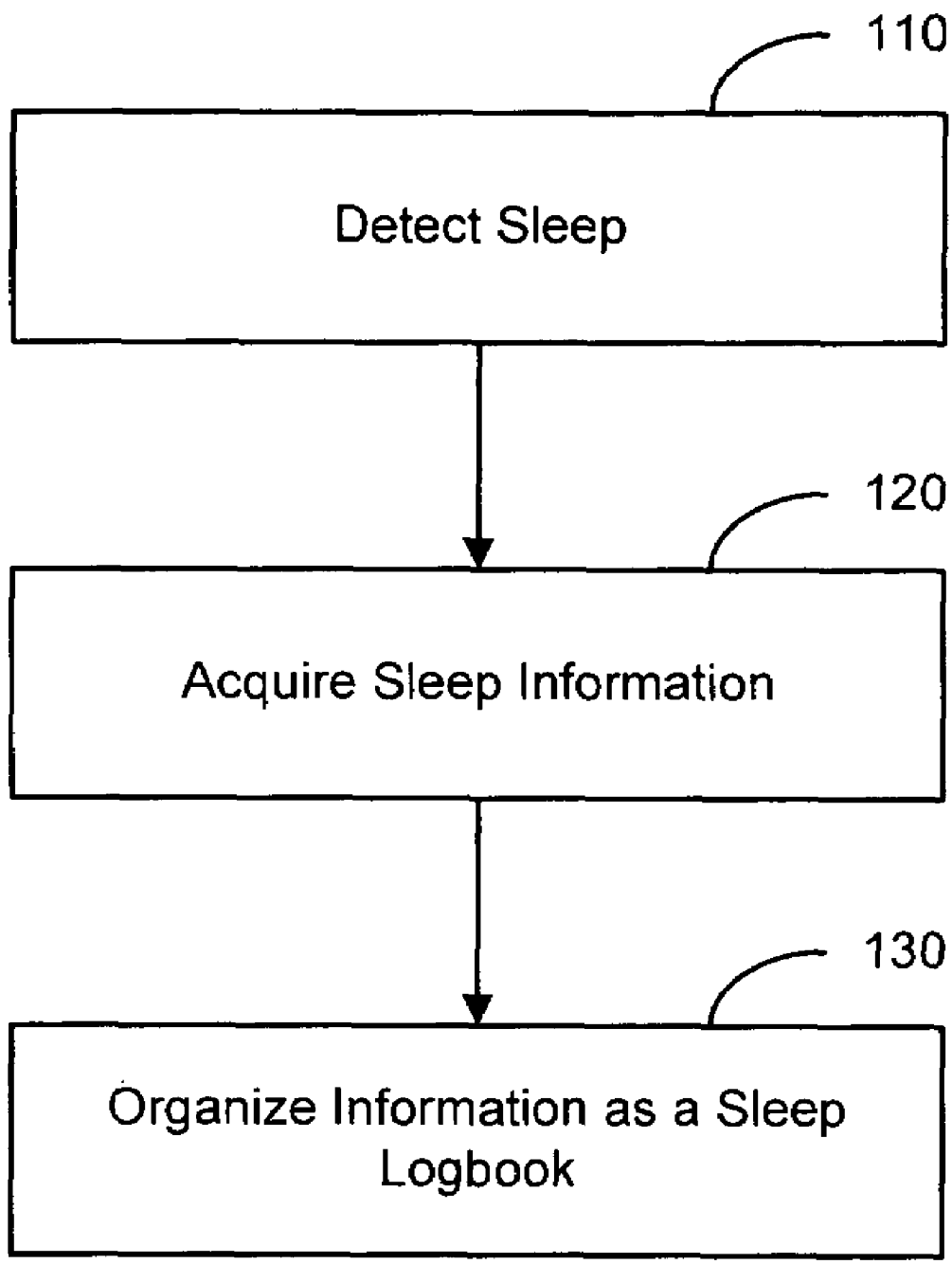
FIG. 1 is a flowchart of a method for acquiring and organizing sleep logbook entry information in accordance with embodiments of the invention.

While the invention is amenable to various modifications and alternative forms, specifics therof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown, by way of illustration, various embodiments by which the invention may be practiced. It is to be understood that other embodiments may be utilized. Structural and functional changes may be made without departing from the scope of the present invention.

Sleep quality assessments depend upon acquiring sleep-related data, including the patient's typical sleep patterns and the physiological, environmental, contextual, emotional, and other conditions affecting the patient during sleep. Diagnosis of sleep disorders and assessment of sleep quality often involves the use of a polysomnographic sleep study at a dedicated sleep facility. However, such studies are costly, inconvenient to the patient, and may not accurately represent the patient's typical sleep behavior. In a polysomnographic sleep study, the patient is instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Further, polysomnographic sleep studies provide an incomplete data set for the analysis of some sleep disorders, including, for example, sleep disordered breathing. A number of physiological conditions associated with sleep disordered breathing are detectable during periods of wakefulness, e.g., decreased heart rate variability, elevated sympathetic nerve activity, norepinephrine concentration, and increased blood pressure variability. Collection of data during periods of sleep and/or during periods of wakefulness may provide a more complete picture of the patient's sleep quality.

Various aspects of sleep quality, including the number and severity of arousals, sleep disordered breathing episodes, and nocturnal limb movements. Further, cardiac, respiratory, muscle, and nervous system functioning may provide important information for diagnosis and/or therapy delivery. An initial step to sleep quality evaluation is an accurate and reliable method for discriminating between periods of sleep and periods of wakefulness. Further, acquiring data regarding the patient's sleep states or stages, including sleep onset, termination, REM, and NREM sleep states may be used in connection sleep quality assessment. For example, the most restful sleep occurs during stages 3 and 4 NREM sleep. One indicator of sleep quality is the percentage of time a patient spends in these sleep stages. Knowledge of the patient's sleep patterns may be used to diagnose sleep disorders and/or adjust patient therapy, including, e.g., cardiac or respiratory therapy. Trending disordered breathing episodes, arousal episodes, and other sleep quality aspects may be helpful in determining and maintaining appropriate therapies for patients suffering from disorders ranging from snoring to congestive heart failure. Methods and systems for detecting arousals from sleep including autonomic arousals, aspects of which may be implemented in connection with the embodiments discussed herein, are described in commonly owned U.S. patent application Ser. No. 10/920,675 entitled "Autonomic Arousal Detection System and Method," filed concurrently with this application and incorporated herein by reference.

Embodiments of the invention are directed to methods and systems for automatically acquiring and organizing sleep information as a sleep logbook. FIG. 1 illustrates a flowchart of a method for acquiring and organizing sleep data. The method involves detecting 110 a period of sleep and acquiring 120 information associated with the period of sleep. The acquired sleep information is organized as a sleep logbook entry 130. At least one of detecting the period of sleep, acquiring the sleep information, and organizing the information is performed at least in part implantably. Implantably performing an operation comprises performing the operation using a component, device, or system that is partially or fully implanted within the body.

The sleep logbook represents a system for organizing sleep-related data. According to one embodiment, each sleep logbook entry may include data associated with a particular sleep-related event. An event may comprise various types of events related to sleep. The types of information acquired and the types of sleep-related events represented in the sleep logbook may be programmable by a user.

According to an embodiment of the invention, information may be collected continuously or periodically throughout a sleep period, e.g., throughout a patient's typical sleep time, or during one or more particular sleep stages. The system may initiate acquisition of information before, during and/or after detection of sleep or detection of a particular sleep stage. In this example, each sleep period for which data is collected may be organized as a sleep logbook entry.

The system may initiate acquisition of information responsive to the detection or prediction of an event occurring during sleep. In this example, data associated with each event occurring during sleep may be organized as a sleep logbook entry. The system may collect data during the event and proximate in time to the event. For example, data may be collected before, during, and/or after the detected or predicted event. Methods and systems for predicting a sleep disordered breathing event, aspects of which may be utilized in connection with implementing a sleep logbook, are described in commonly owned U.S. patent application Ser. No. 10/643,016, filed Aug. 18, 2003, now U.S. Pat. No. 7,396,333, which is incorporated herein by reference.

In various embodiments, the acquisition of information may be controlled responsive to triggering events. In this embodiment, the system may start acquiring the information associated with sleep, stop acquiring the information, or continue to acquire the information in response to a triggering event. A triggering event may include, for example, one or more of a physiological event, a non-physiological event, a cardiovascular system event, respiratory system event, nervous system event, muscle system event, sleep-related event, disordered breathing event, sleep stage, or other events.

The sleep logbook acquires information about one or more conditions related to sleep and/or sleep quality. A representative set of the conditions associated with sleep and/or sleep quality is listed in Table 1. Patient conditions used to evaluate sleep and sleep quality may include, for example, both physiological and non-physiological (i.e., contextual) conditions. Physiological conditions associated with sleep may be further organized, for example, into conditions of the cardiovascular, respiratory, muscle, and nervous systems, and conditions relating to the patient's blood chemistry. Systems and methods for acquiring and evaluating information related to sleep quality, aspects of which may be utilized in connection with embodiments of the present invention, are described in U.S. patent application Ser. No. 10/642,998, filed Aug. 18, 2003, now U.S. Publication No. 2005/0042589, and incorporated herein by reference.

Non-physiological conditions may be further subdivided into environmental conditions, body-related conditions and historical/background conditions. Environmental conditions may be broadly defined to include the environmental surroundings affecting the patient, such as ambient light, temperature, humidity, air pollution, noise, and barometric pressure. Body-related conditions may include, for example, patient location, posture, and altitude. Non-physiological conditions relevant to sleep quality may also include historical or background conditions. For example, a patient's medical/psychological history, gender, age, weight, body mass index, neck size, drug use, and emotional state may be detected and used in connection with sleep quality evaluation and sleep disorder diagnosis. Methods and systems for detecting contextual conditions are described in commonly owned U.S. patent application Ser. No. 10/269611, filed Oct. 11, 2002, now U.S. Pat. No. 7,400,928, which is incorporated herein by reference.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | $CO_2$ saturation | Blood analysis |
| | | $O_2$ saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |
| | Muscle System | Muscle atonia | Electromyogram (EMG) |
| | | Eye movement | Electrooculogram (EOG) |
| | | Patient activity | Accelerometer, MV, etc. |
| | | Limb movements | Accelerometer |
| | | Jaw movements | |
| Non-physiological | Environmental | Ambient temperature | Thermometer |
| | | Humidity | Hygrometer |
| | | Pollution | Air quality website |
| | | Time | Clock |
| | | Date | Clock |
| | | Barometric pressure | Barometer |
| | | Ambient noise | Microphone |
| | | Ambient light | Photodetector |
| | Body-related | Posture | Posture sensor |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input device |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

Each of the conditions listed in Table 1 may serve a variety of purposes in evaluating sleep and/or sleep quality. For example, a subset of the conditions may be used to detect whether the patient is asleep and to track the various stages of sleep and arousal incidents. Another subset of the conditions may be used to detect disordered breathing episodes. Yet another subset may be used to detect abnormal limb movements. In one implementation, the sleep logbook may comprise a number of sleep logbook entries acquired over a relatively long period of time. The multiple sleep logbook entries may be used to analyze long term sleep trends. Trending may be used in connection with an overall. assessment of sleep quality and diagnosis and treatment of sleep-disordered breathing, movement disorders, and/or other sleep disorders.

In one implementation, the information acquired and organized by the sleep logbook may be used within the structure of an advanced patient management system. In one implementation, an advanced patient management system coupled to the sleep logbook system described herein allows a physician to remotely and automatically monitor cardiac and respiratory functions, as well as other patient conditions, including information related to sleep quality. In one example, an implantable cardiac rhythm management system, such as a cardiac monitor, pacemaker, defibrillator, or cardiac resynchronization device, may be equipped with various telecommunications and information technologies to enable real-time data collection, diagnosis, and treatment of the patient. Systems and methods involving advanced patient management techniques are described in U.S. Pat. Nos. 6,336,903, 6,312,378, 6,270,457, and 6,398,728 which are incorporated herein by reference in their respective entireties.

Table 2 provides examples of how some physiological and non-physiological conditions may be used in connection with sleep quality assessment.

TABLE 2

| Condition Type | Condition | Examples of how condition is used in sleep quality assessment |
|---|---|---|
| Physiological | Heart rate | Decrease in heart rate may indicate disordered breathing episode. |
| | | Decrease in heart rate may indicate the patient is asleep. |
| | Heart rate variability | May be used to determine sleep state. Changes in heart rate variability, detected during periods of sleep or wakefulness, may indicate that the patient suffers from sleep disordered breathing. |
| | QT interval | May be used to detect sleep apnea. |
| | Ventricular filling pressure | May be used to identify/predict pulmonary congestion associated with respiratory disturbance. |
| | Blood pressure | Variation in blood pressure is associated with apnea. |
| | Snoring | Associated with a higher incidence of obstructive sleep apnea and may be used to detect disordered breathing. Snoring indicates the patient is asleep. |
| | Respiration pattern | May be used to detect disordered breathing episodes. |
| | | May be used to determine the type of disordered breathing. |
| | | May be used to detect sleep. |
| | Patency of upper airway | Related to obstructive sleep apnea and may be used to detect episodes of obstructive sleep apnea. |
| | Pulmonary congestion | Associated with respiratory disturbances. |
| | Sympathetic nerve activity (SNA) | Apnea termination is associated with a spike in SNA. |
| | | SNA activity may be elevated during periods of wakefulness if the patient experiences sleep disordered breathing. |
| | Electroencephalogram (EEG) | May be used to detect sleep. |
| | | May be used to detect arousals from sleep. |
| | | May be used to determine sleep stages, including REM and NREM sleep stages |
| | $CO_2$ saturation | Low $CO_2$ levels may indicate initiation of central apnea. |
| | | May be used to predict central apnea risk. |
| | $O_2$ saturation | $O_2$ desaturation occurs during severe apnea/hypopnea episodes. |
| | | May be used to evaluate presence and severity of sleep disordered breathing event. |
| | Blood alcohol content | Alcohol tends to increase the incidence of snoring & obstructive apnea. |
| | Adrenalin | End of apnea associated with a spike in blood adrenaline. |
| | Brain Natriuretic Peptide (BNP) | A marker of heart failure status, which is associated with Cheyne-Stokes Respiration. |
| | C-Reactive Protein | A measure of inflammation that may be related to apnea. |
| | Drug/ Medication/ Tobacco use | These substances may affect incidence of both central & obstructive apnea. |

TABLE 2-continued

| Condition Type | Condition | Examples of how condition is used in sleep quality assessment |
|---|---|---|
| | Muscle atonia | Muscle atonia may be used to discriminate REM from non-REM sleep. |
| | Eye movement | Eye movement may be used to discriminate REM from non-REM sleep. |
| | Activity | May be used to detect sleep and patient well being. |
| | Limb movements | May be used to detect abnormal limb movements during sleep. |
| Non-physiological | Ambient Temperature | Ambient temperature may predispose the patient to episodes of disordered breathing during sleep. |
| | Humidity | Humidity may predispose the patient to episodes of disordered breathing during sleep. |
| | Pollution | Pollution may predispose the patient to episodes of disordered breathing during sleep. |
| | Posture | Posture may be used to determine if the patient is asleep. |
| | | Posture may predispose the patient to disordered breathing. |
| | Time | Used to establish historical sleep time. |
| | Ambient noise level | Noise level may affect sleep quality. |
| | Location | Patient location may used to determine if the patient is in bed as a part of sleep detection. |
| | Altitude | Altitude may predispose the patient to episodes of disordered breathing and may affect sleep quality. |
| | Barometric Pressure | Barometric pressure may predispose the patient to episodes of disordered breathing. |
| | Proximity to bed | May be used to determine if patient is in bed. |
| | Historical sleep time | May be used in connection with sleep detection. |
| | Medical history | History of medical disorders, e.g., CHF, that are associated with disordered breathing such as Cheyne-Stokes respiration. |
| | Age | Age is associated with increased risk of disordered breathing, RLS and other sleep disruptive disorders. |
| | Weight Gender Obesity Neck size | Associated with sleep disordered breathing, e.g., obstructive sleep apnea. |
| | Patient reported drug, alcohol, nicotine use | Patient drug, alcohol and nicotine use may affect sleep quality. |
| | Psychological history | Psychological factors, e.g., clinical depression may be associated with insomnia. |
| | Emotional state | Emotional state, e.g., stress, anxiety, euphoria, may affect sleep quality. |
| | Daytime sleepiness | May be used to evaluate sleep quality. |
| | Patient perceptions of sleep quality | |

The sleep logbook may comprise a number of entries, each entry corresponding to a separate sleep period. The sleep logbook entries included in the sleep logbook may be organized and/or accessed in various ways, including for example, chronologically, by type of events detected during the sleep period, by event severity, by new-onset event types, by metrics calculated corresponding to the sleep period, or by other organizational schema. For example, the sleep logbook entries may be organized and/or accessed based on apnea/hypopnea index associated with the sleep period, by arousal index, by undisturbed sleep efficiency metric associated with the sleep period, or by other detected or derived characteristics of the sleep period. The selection of categories used to organize the information may be programmable by the user. The organized information may be stored in memory, displayed, printed, and/or transmitted to a separate device.

The information collected for the sleep periods may be accessible though an interactive user interface involving a hierarchical selection menu, or other selection method, for example. In one implementation, the user may select a sleep logbook entry from the menu by activating an input mechanism. Upon selection of the logbook entry, the user interface may provide graphical or textual depictions of the collected information associated with the sleep period.

In addition to accessing information related to sleep, the user interface of the sleep logbook may also provide access to other types of information. The sensors and other data collection circuitry of the sleep logbook system may be used to collect data other than sleep-related data. The data may be stored, transmitted, displayed, or otherwise processed. The user interface of the sleep logbook may provide access to medical information collected about physiological conditions/events and/or non-physiological conditions/events that are not necessarily related to sleep. Systems and methods for providing a medical event logbook are described in commonly owned U.S. patent application Ser. No. 10/920,675 entitled "Medical Event Logbook System and Method," now U.S. Publication No. 2005/0080348, filed concurrently with this application and incorporated herein by reference. The sleep logbook user interface may be configured to provide access to information related to diagnostics and/or therapy used to treat the patient for sleep disorders and/or other types of disorders, e.g., cardiac disorders, respiratory disorders, etc.

In one implementation, the sleep logbook user interface provides access to sleep-related information as well as information about cardiovascular system conditions or events, e.g., bradycardia, tachyarrhythmia, ischemia, and/or other physiological conditions related to the patient's cardiovascular system. The user interface may further allow access to therapy and/or diagnostic information for sleep-related disorders as well as other disorders, such as the cardiovascular system disorders referred to above. In one implementation, the sleep logbook user interface may be used to access to congestive heart failure (CHF) diagnostic information and information about cardiac resynchronization therapy delivered to the patient to treat CHF, for example.

The information collected by the sleep logbook may be stored in memory using various storage methodologies. For example, the sleep logbook may utilize a flat file system, hierarchical database, relational database, or distributed database. Data for a group of events may be analyzed and/or summarized in various formats. Graphical and/or textual summary information may be displayed on the user interface and/or otherwise communicated to the user. For example, histograms, trend graphs, and/or other analytical tools or formats may be generated based on the logbook event entries. A sleep logbook display may have the ability to display trends of the patient's, arousal index, apnea/hypopnea index, histograms of number of apneas/hypopneas and/or obstructive/central events per night, sleep stage diagram (shows the stage of sleep for each night), heart rate trend during the night, oxygen saturation trend during the night, or other parameters.

Figure 2:
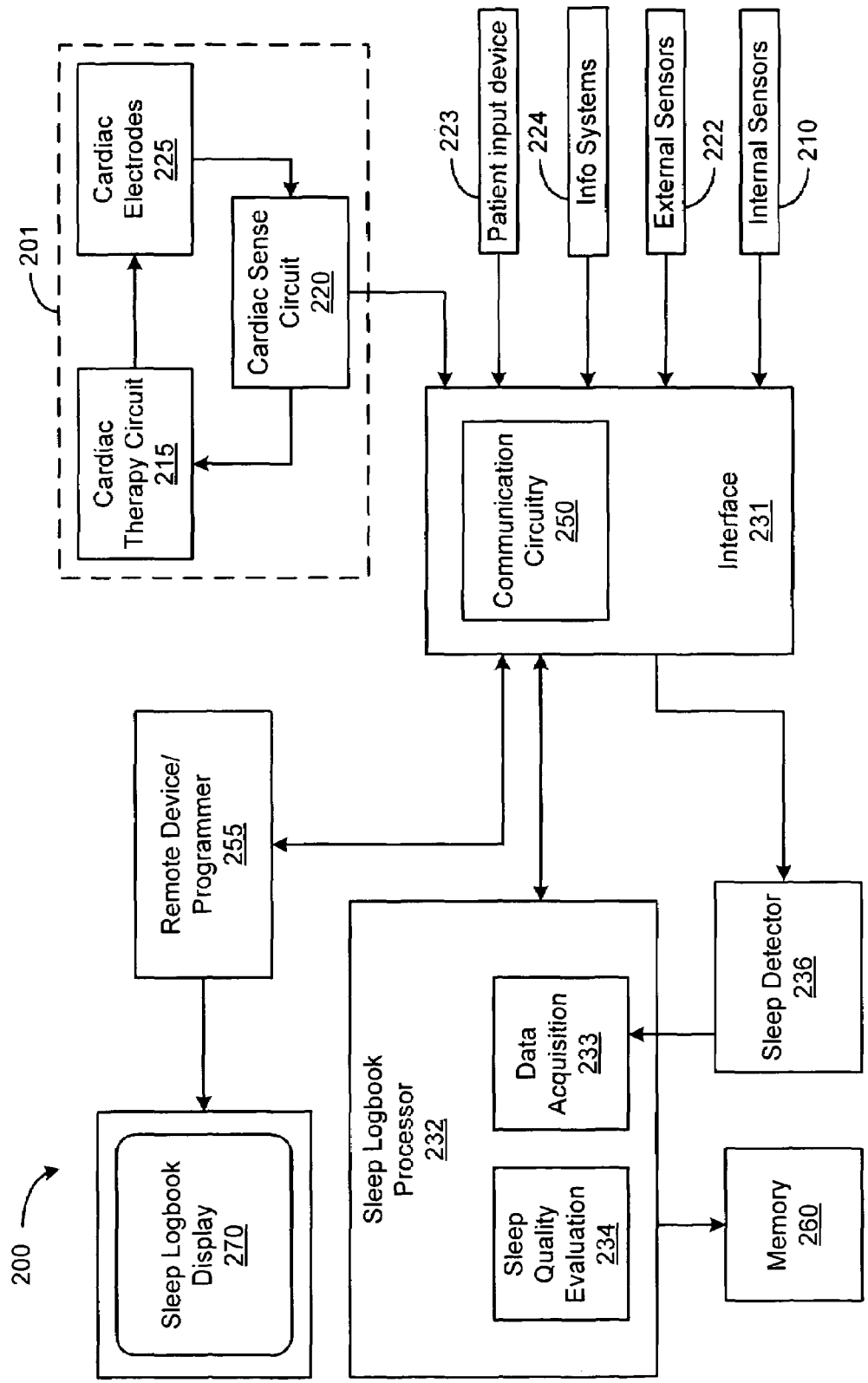
FIG. 2 is a block diagram of a sleep logbook system in accordance with embodiments of the invention.

FIG. 2 is a block diagram of a sleep logbook system 200 in accordance with embodiments of the invention. In this exemplary embodiment, the system includes sleep logbook functionality provided along with a cardiac rhythm management. This embodiment is particularly useful for patients benefiting from cardiac pacing and/or defibrillation support through an implantable cardiac pulse generator.

Various patient conditions associated with sleep may be monitored through sensors 222, patient input devices 223, and/or information systems 224. One or more of the patient conditions may be used by sleep detection circuitry 236 to detect the onset and/or offset of sleep. Detection of sleep onset initiates the collection of information associated with the sleep period by the data acquisition unit 233 of a sleep logbook processor 232. For example, the data acquisition unit 233 may collect information supplied by one or more of the sensors 222, patient input devices 223, and information systems 224 before, during, and/or after the sleep period. The collected information associated with each sleep period is organized as a sleep logbook entry in the sleep logbook. The sleep logbook, or portions thereof, may be stored in memory 260, transmitted to a remote device 255, and/or displayed on a display device 270.

The embodiment illustrated in FIG. 2 may include, for example, a respiration sensor that senses a physiological condition modulated by patient respiration. In one embodiment, the respiration sensor may comprise an implantable transthoracic impedance sensor. Other methods of sensing respiration are also possible. Such methods may include, for example, the use of patient-external respiratory bands, respiration flowmeter measurements, implantable or patient-external breath sound detection, blood oxygen levels, and/or other processes. The respiration sensor may acquire information used in the detection of sleep onset and offset, as described in greater detail below. Additionally or alternatively, respiration sensing may be used, for example, to acquire a respiration waveform before, during, and/or after an event affecting the patient respiration. The respiration waveform may be a component of the sleep logbook entry.

Information about various conditions associated with and/or occurring during sleep may be acquired using sensors 222, patient input devices 223 and/or other information systems 224. The sensors 222 may comprise patient-internal and/or patient-external sensors coupled through leads or wirelessly to the interface 231 of the sleep logbook system 200. The sensors may sense various physiological and/or non-physiological conditions. The patient input device 223 allows the patient to input information relevant to conditions affecting the patient that may be useful in generating a sleep log. For example, the patient input device 223 may be particularly useful for acquiring information known to the patient, such as information related to patient smoking, drug use, recent exercise level, and/or other patient activities, symptoms, or perceptions, including patient perceptions of daytime sleepiness and/or sleep quality. The information provided by the patient-input device may include patient-known information that is not automatically sensed or detected by the sleep logbook system 200.

The sleep logbook system 200 may also include one or more information systems 224 such as a remote computing device and/or a network-based server. The event information processor 232 may access the information systems 224 to acquire information from databases and/or other information sources stored on or generated by the remote computing devices and/or servers. The information acquired from the information systems 224 may be recorded in the sleep logbook along with other information relevant to the event affecting sleep. In one exemplary implementation, the sleep logbook system 200 may access an internet connected air quality server to collect data related to environmental conditions, such as an ambient pollution index. In another implementation, the sleep logbook system 200 may access the patient's medical history through a patient information server.

The sensors 222, patient input devices 223, and information systems 224 are coupled to other components of the sleep logbook system 200 through interface circuitry 231. The interface 231 may include circuitry for energizing the sensors 222 and/or for detecting and/or processing signals generated by the sensors. The interface 231 may include, for example, driver circuitry, amplifiers, filters, sampling circuitry, and/or A/D converter circuitry for conditioning the signals generated by the sensors.

The interface 231 may also include circuitry 250 for communicating with the patient input device 223, information systems 224, a device programmer 255, an APM system (not shown), or other remote devices. Communication with the patient input device 223, information systems 224 and/or a remote device programmer 255 and/or other remote devices may be implemented using a wired connection or through a wireless communication link, such as a Bluetooth or other proprietary wireless link. The communication circuitry 250 may also provide the capability to wirelessly communicate with various sensors, including implantable, subcutaneous, cutaneous, and/or external sensors.

The sleep logbook functionality may optionally be provided in a medical device that includes a therapy system, such as an implantable cardiac rhythm management system 201. The cardiac rhythm management system 201 may include cardiac electrodes 225 electrically coupled to the patient's heart. Cardiac signals sensed by cardiac sense circuitry 220 may be used in the detection and treatment of various anomalies of the heart rhythm. Anomalous heart rhythms may include, for example, a rhythm that is too slow (bradycardia), a heart rhythm that is too fast (tachycardia), and/or a heart rhythm that involves insufficiently synchronized contractions of the atria and/or ventricles, a symptom of congestive heart failure.

If an arrhythmia is detected by the cardiac rhythm management system, then a cardiac therapy circuit 215 may deliver cardiac therapy to the heart in the form of electrical stimulation pulses, such as pacing and/or cardioversion/defibrillation pulses. The cardiac signals and/or cardiac conditions, e.g., arrhythmia conditions, derived or detected through the use of the cardiac signals may be associated with sleep. The cardiac information associated with sleep may be acquired and organized by the sleep logbook system 200.

Figure 3:
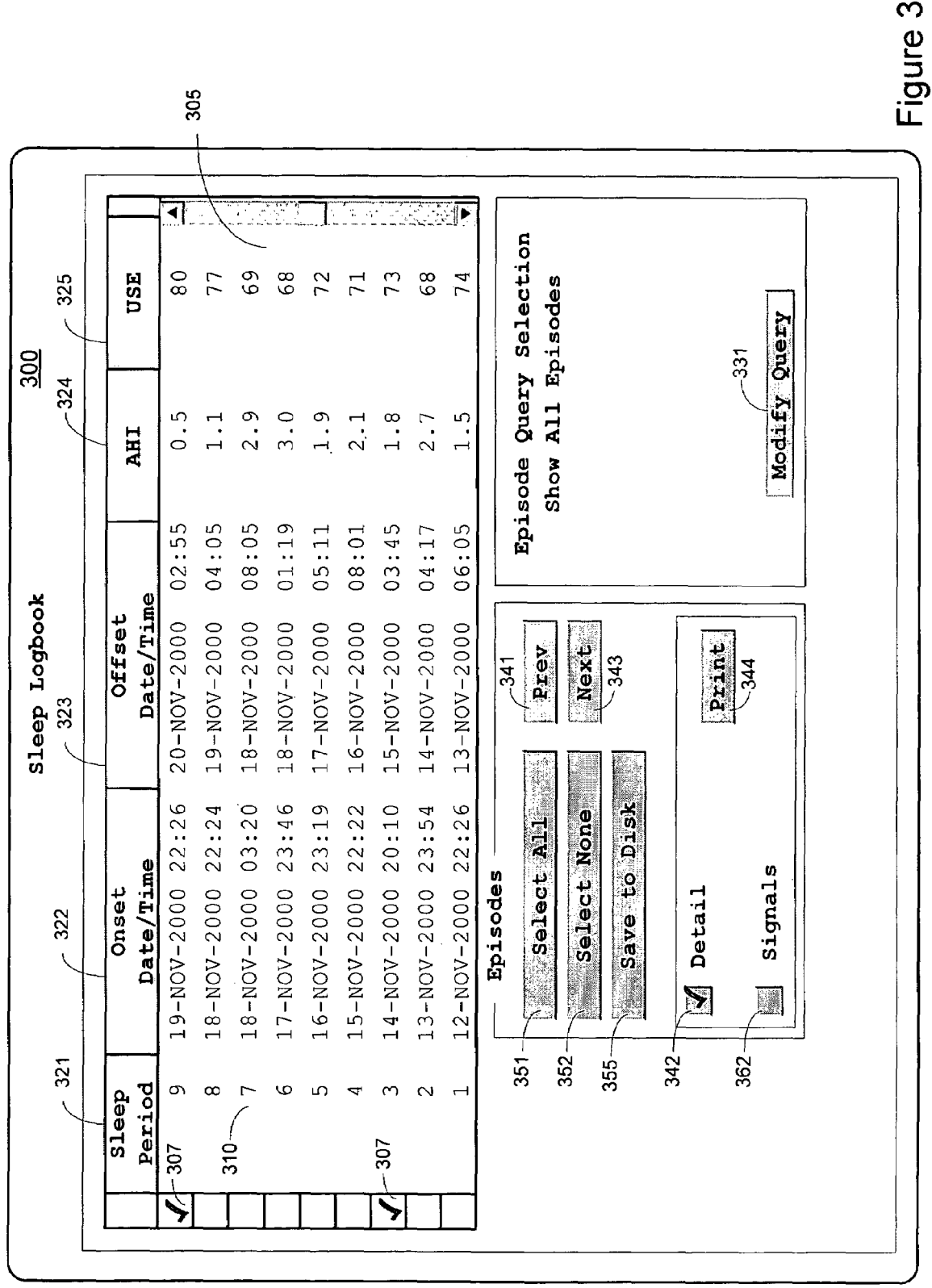
FIG. 3 illustrates an exemplary depiction of a user interface display that may be used with a sleep logbook system in accordance with embodiments of the invention.

A user interface may be used to view and/or access the sleep logbook information. FIG. 3 illustrates an exemplary depiction of a user interface display 300. An area 305 of the display may be used to provide textual or graphical information about sleep. As illustrated in FIG. 3, a menu 310 of sleep periods may be presented and may enable the user to access additional information related to the sleep periods and/or to sleep disorder events occurring during the. sleep periods. The menu 310 may provide a summary of parameters associated with sleep periods contained in the sleep logbook. As illustrated in FIG. 3, one or more summary parameter headings, such as sleep period 321, onset date/time 322, offset date/time 323, apnea/hypopnea index (AHI) 324, uninterrupted sleep efficiency 325, among other parameter headings, may be presented at the top of the menu 310 or in another convenient location. The summary parameter headings 321-325 may be programmable, and additional or alternative parameter headings to those depicted in FIG. 3 may be selected.

The sleep periods displayed as menu items in the menu 310 may be selected by a user according to episode number, date/time, duration, or by other criteria such as by one or more sleep quality indices. Additionally or alternatively, the menu items may reflect one or more sleep disorder events, e.g., movement disorder events and/or disordered breathing events. The menu items may be selected for display based on various criteria ranges and/or thresholds. For example, in the example screen illustrated in FIG. 3, different groups of sleep periods selected as menu items may be selected by activating the modify query button 331. In an alternate scenario, different groups of sleep disorder events selected as menu items may be selected by activating the modify query button 331. The modify query button 331 and other buttons illustrated on the display may be voice activated, activated through touching the display screen, or by operating a keyboard or pointing device, for example.

In one implementation, activation of the modify query button 331 initiates a dialog session that allows the user to select sleep periods and/or sleep disorder events to be presented in the menu according various criteria such as by date/time, duration, type, sleep quality metrics, or by other criteria parameters. In one example, the user may select all sleep periods having an uninterrupted sleep efficiency (USE) metric below a threshold to be presented as menu items. In another example, the user may select all sleep periods between a first date and a second date. In yet another example, the user may select all sleep disorder events of a particular type that occurred while the patient experienced certain environmental conditions, e.g., ambient temperature range and/or humidity range. In yet another example, the user may choose to select all sleep periods or all sleep disorder events represented in the sleep logbook. The selection criteria may be displayed in an episode query selection area 332 of the display. The episode query selection area 332 in the depiction of a sleep logbook display shown in FIG. 3 indicates that all sleep periods have been selected to be displayed as menu items.

The menu 310 allows the user to choose sleep periods for which additional textual and/or graphical information is displayed. The additional information provides more detailed information about the selected periods beyond the summary information presented in the menu 310. In the exemplary illustration depicted in FIG. 3, the selections are indicated by check marks 307 beside the selected sleep periods. For convenience, the display may include a select all button 351 and/or a select none button 352. Activation of the select all button 351 causes all sleep periods in the menu 310 to be selected. Activation of the select none button 352 causes all sleep periods in the menu 310 to be deselected.

Following selection of one or more sleep periods in the menu, activation of the detail button 342 causes detailed textual information associated with a selected sleep period to be presented on the display screen. The detail information may be displayed in the area of the screen 305 previously occupied by the menu 310, for example. The user may scroll back and forth through the textual information for the one or more selected sleep periods using the prev button 341 and the next button 343. The textual information may be printed upon activation of the print button 344, or may be saved to a disk, or other storage medium, through activation of the save to disk button 355.

Graphical information associated with the selected sleep periods may be displayed upon activation of the signals button 362. In one implementation, a respiration waveform acquired during all or a portion of a selected sleep period may be displayed in the area 305 of the display previously used for the menu 310. In one implementation, a respiration waveform may be acquired before, during and/or after respiration events that occur during sleep. Waveforms of other parameters, e.g., cardiac rhythm, patient activity, may additionally or alternatively be displayed. In one implementation, a marked waveform may be displayed. For example, a marked respiration waveform may include the respiration waveform along with one or more symbols aligned with the respiration waveform to indicate the occurrence of one or more conditions. The symbols may provide a numerical value or a textual description associated with the respiration characteristic, e.g., average respiration rate, expiratory slope, etc. In one example, various characteristics of disordered breathing events including quantifiable characteristics, such as episode duration, blood oxygen saturation, disordered breathing type, and/or other detected characteristics may also be displayed along with the respiration waveform. A user may scroll through the waveforms associated with the selected events using the prev and next buttons 341, 343.

Figure 4:
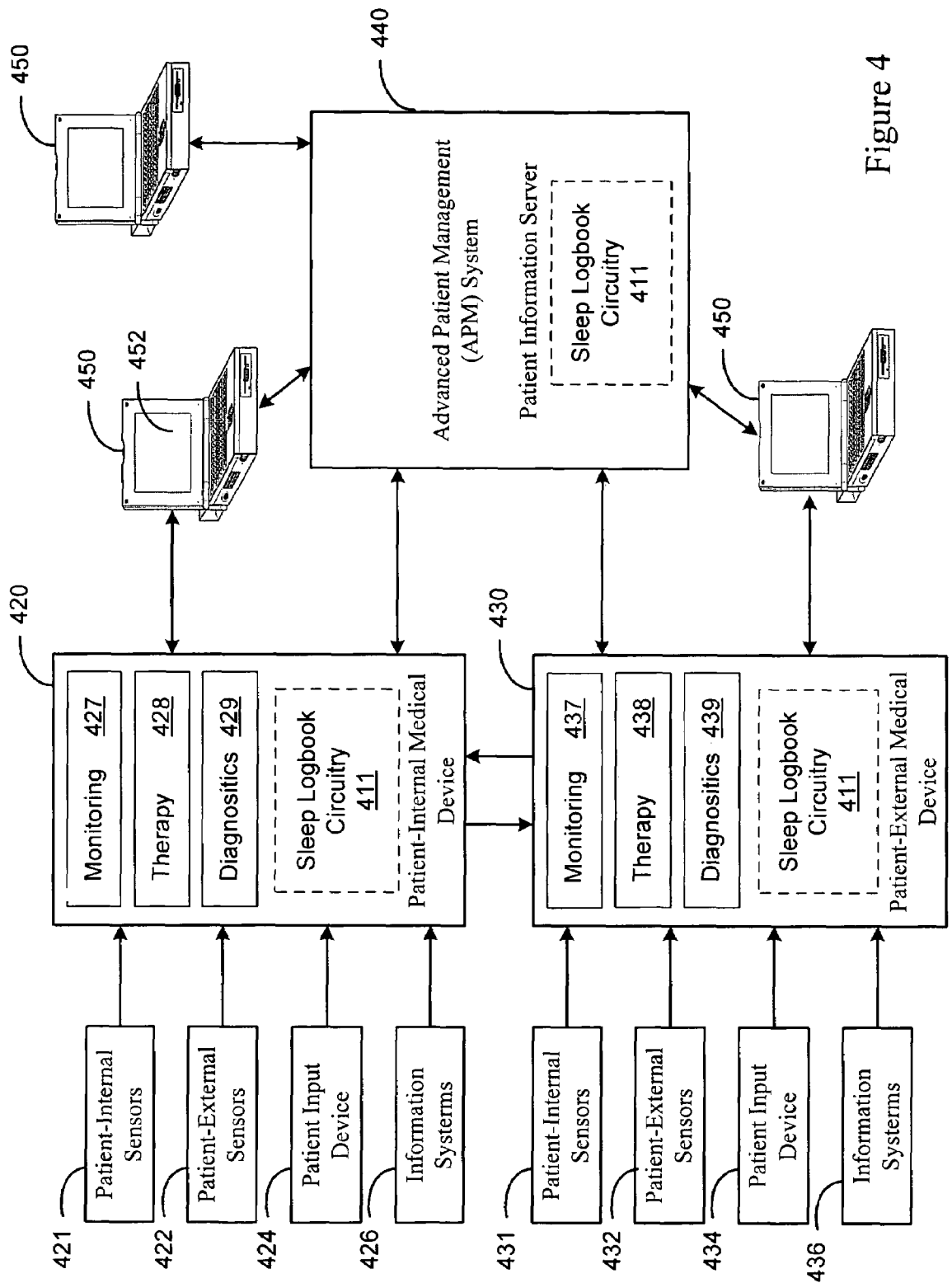
FIGS. 4 and 5 are block diagrams of medical systems that may be used to implement a sleep logbook system in accordance with embodiments of the invention.

FIG. 4 is a block diagram of a medical system that may be used to implement a sleep logbook system in accordance with embodiments of the invention. The medical system may include, for example, one or more patient-internal medical devices 420 and one or more patient-external medical devices 430. Each of the patient-internal 420 and patient-external 430 medical devices may include one or more of a patient monitoring unit 427, 437, a diagnostics unit 429, 439, and/or a therapy unit 428, 438. Sleep logbook circuitry 411, as described more fully in connection with FIG. 2 above, including an external device interface, sleep detector, sleep information processor and/or memory, for example, can be housed in a patient internal medical device 420, a patient external medical device 430, a remote system such as advanced patient medical (APM) system 440 or in any combination of the above-mentioned devices 420, 430, 440.

The patient-internal medical device 420 may be a fully or partially implantable device that performs monitoring, diagnosis, and/or therapy functions. The patient-external medical device 430 may perform monitoring, diagnosis and/or therapy functions external to the patient (i.e., not invasively implanted within the patient's body). The patient-external medical device 430 may be positioned on the patient, near the patient, or in any location external to the patient. It is understood that a portion of a patient-external medical device 430 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 420, 430 may be coupled to one or more sensors 421, 422, 431, 432, patient input devices 424, 434 and/or other information acquisition devices 426, 436. The sensors 421, 422, 431, 432, patient input devices 424, 434, and/or other information acquisition devices 426, 436 may be employed to detect conditions relevant to the monitoring, diagnostic, and/or therapeutic functions of the patient-internal and patient-external medical devices 420, 430.

The medical devices 420, 430 may each be coupled to one or more patient-internal sensors 421, 431 that are fully or partially implantable within the patient. The medical devices 420, 430 may also be coupled to patient-external sensors 422, 432 positioned on the patient, near the patient, or in a remote location with respect to the patient. The patient-internal 421, 431 and patient-external 422, 432 sensors may be used to sense conditions, such as physiological and/or non-physiological conditions, that affect the patient.

The patient-internal sensors 421 may be coupled to the patient-internal medical device 420 through implanted leads. In one example, an internal endocardial lead system is used to couple sensing electrodes to an implantable pacemaker or other cardiac rhythm management device. One or more of the patient-internal sensors 421, 431 may be equipped with transceiver circuitry to support wireless communication between the one or more patient-internal sensors 421, 431 and the patient-internal medical device 420 and/or the patient-external medical device 430.

The patient-external sensors 422, 432 may be coupled to the patient-internal medical device 420 and/or the patient-external medical device 430 through leads or through wireless connections. Patient-external sensors 432 preferably communicate with the patient-internal medical device 420 wirelessly. Patient-external sensors 432 may be coupled to the patient-external medical device 430 through leads or through a wireless link.

The medical devices 420, 430 may be coupled to one or more patient-input devices 424, 434. The patient-input devices 424, 434 facilitate manual transfer of information to the medical devices 420, 430 by the patient. The patient input devices 424, 434 may be particularly useful for inputting information concerning patient perceptions, such as how well the patient feels, sleep quality perceptions, and patient-known information such as patient smoking, drug use, or other activities that are not automatically sensed or detected by the medical devices 420, 430. In one implementation, a device programmer may be used to facilitate patient input to a medical device 420, 430.

The medical devices 420, 430 may be connected to one or more information systems 426, 436, for example, a database that stores information useful in connection with the monitoring, diagnostic, or therapy functions of the medical devices 420, 430. In one implementation, one or more of the medical devices 420, 430 may be coupled through a network to an information system server that provides information about environmental conditions affecting the patient, e.g., the pollution index for the patient's location.

In one embodiment, the patient-internal medical device 420 and the patient-external medical device 430 may communicate through a wireless link between the medical devices 420, 430. For example, the patient-internal and patient-external devices 420, 430 may be coupled through a short-range radio link, such as Bluetooth or a proprietary wireless link. The communications link may facilitate uni-directional or bidirectional communication between the patient-internal 420 and patient-external 430 medical devices. Data and/or control signals may be transmitted between the patient-internal 420 and patient-external 430 medical devices to coordinate the functions of the medical devices 420, 430.

In one embodiment, the patient-internal and patient-external medical devices 420, 430 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

The patient-internal medical device 420 and the patient-external medical device 430 may be coupled through a wireless or wired communications link to a patient information server that is part of an advanced patient management system 440. The APM patient information server 440 may be used to download and store data collected by the patient-internal and patient-external medical devices 420, 430.

The data stored on the APM patient information server 440 may be accessible by the patient and the patient's physician through terminals 450, e.g., remote computers located in the patient's home or the physician's office. The APM patient information server 440 may be used to communicate to one or more of the patient-internal and patient-external medical devices 420, 430 to effect remote control of the monitoring, diagnosis, and/or therapy functions of the medical devices 420, 430.

In one scenario, the patient's physician may access patient data transmitted from the medical devices 420, 430 to the APM patient information server 440. After evaluation of the patient data, the patient's physician may communicate with one or more of the patient-internal or patient-external devices 420, 430 through the APM system 440 to initiate, terminate, or modify the monitoring, diagnostic, and/or therapy functions of the patient-internal and/or patient-external medical systems 420, 430. Systems and methods involving advanced patient management techniques are further described in the previously incorporated U.S. Pat. Nos. 6,336,903, 6,312,378, 6,270,457, and 6,398,728.

In one scenario, the patient-internal and patient-external medical devices 420, 430 may not communicate directly, but may communicate indirectly through the APM system 440. In this embodiment, the APM system 440 may operate as an intermediary between two or more of the medical devices 420, 430. For example, data and/or control information may be transferred from one of the medical devices 420, 430 to the APM system 440. The APM system 440 may transfer the data and/or control information to another of the medical devices 420, 430.

As previously indicated, sleep logbook circuitry 411, including an external device interface, sleep detector, sleep information processor, and memory, for example, can be housed in a patient internal medical device 420, a patient external medical device 430, an advanced patient medical (APM) system 440 or in any combination of the above-mentioned devices. For explanatory purposes, in the following discussion, the sleep logbook circuitry 411 is described as being housed within the patient internal medical device 420. As previously discussed, the patient internal medical device 420 may be coupled to various sensors, 421, 422, patient input devices 424, and/or other information systems 426. These sensing and detection devices may be used to detect conditions relevant to events affecting respiration. One or more patient input devices 424 allow the patient to enter information associated with the events into the medical device 420. Further, a variety of information systems 426 may be accessible by the patient-internal medical device 420, including, for example, network or internet-based information systems. The information systems 426 may provide event-related information such as local pollution levels, local temperature, humidity, etc. For example, the conditions associated with events affecting respiration may be any of the conditions referred to in the tables illustrated in Tables 1-2 or other conditions.

In accordance with various embodiments of the invention, the sleep logbook circuitry 411 may comprise circuitry configured to evaluate one or more patient conditions to detect sleep onset and/or offset. The sleep logbook circuitry initiates the collection of information related to sleep periods. In one scenario, the sleep logbook circuitry may initiate collection of information from sensors 421, 431, 422, 432 or other input devices 424, 434, 426, 436 coupled to any combination of the patient internal medical device, 420 patient-external medical device 430 and a remote device, such as the APM server 440. The respiration logbook circuitry may initiate collection of information associated with any of the patient conditions listed in the tables illustrated in Tables 1-2. Information associated with sleep may be acquired during a period of sleep or while the patient is awake. In various embodiments of the invention, acquired information related to sleep may be transmitted to a separate computing device 430, 440, 450 and/or stored in the patient-internal device 420. The information may be organized and displayed on a display unit 452 as discussed in connection with FIG. 3.

The patient-internal sensors 421, 431, patient-external sensors 422, 432, patient input devices 424, 434, and/or information systems 426, 436 may be used to acquire a variety of information related to sleep either during sleep or while the patient is awake. The acquired information may include both physiological and non-physiological conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Non-physiological conditions generally encompass environmental, body-related or background conditions. Environmental conditions may be broadly defined to include, for example,-present conditions such as, ambient temperature, humidity, and air pollution index. Body-related conditions may include items such as posture and patient location. Non-physiological conditions may also include historical/background conditions relating to the patient, including the patient's normal sleep time and the patient's medical history, for example.

Figure 5:
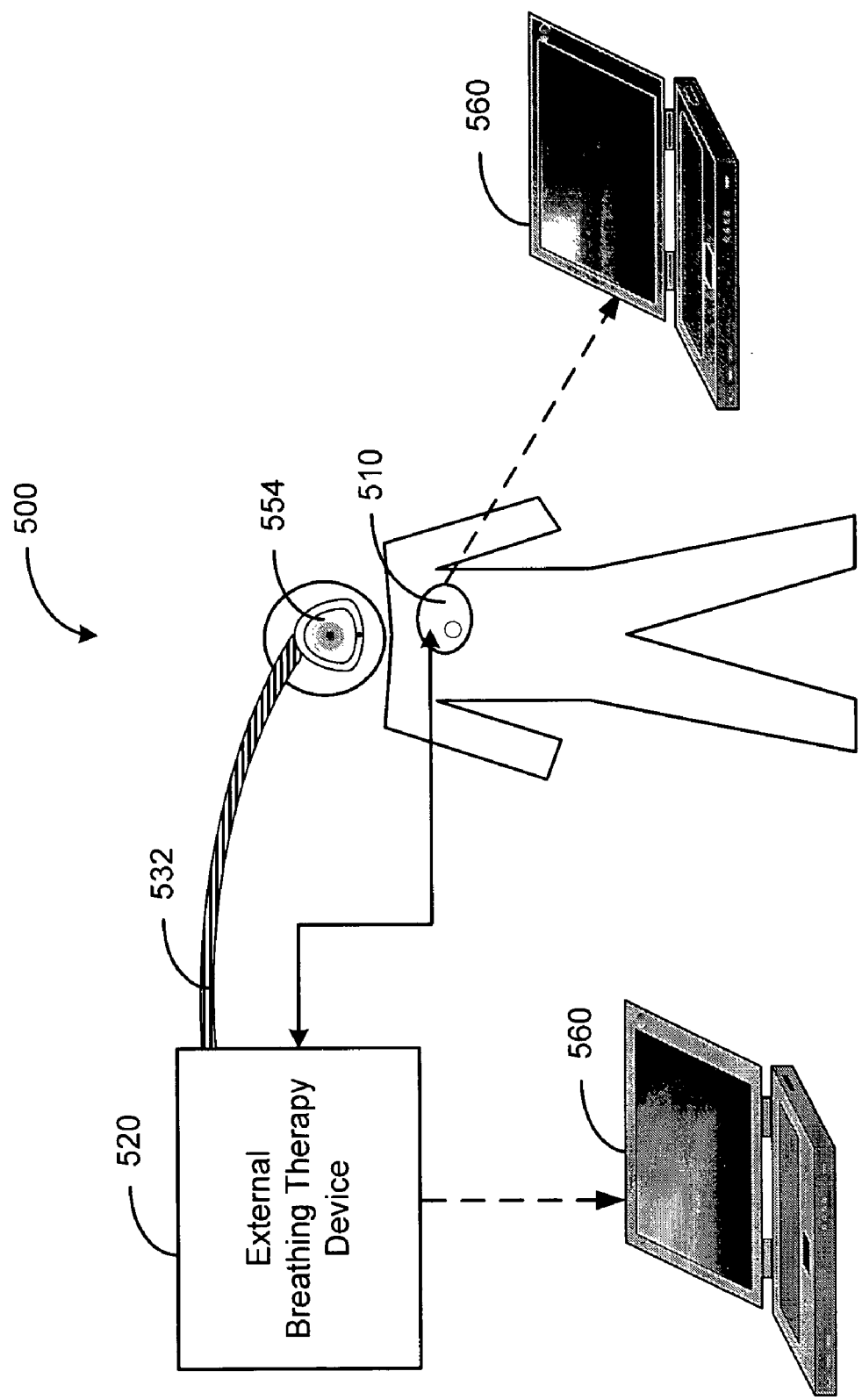

FIG. 5 is a block diagram of a medical system that may be used to implement a sleep logbook system in accordance with embodiments of the invention. In this embodiment, the medical system 500 includes an implantable cardiac device 510 cooperating with an external respiration therapy device 520 to implement a sleep logbook.

In one embodiment, the implantable cardiac device 510 may comprise, for example, an implantable cardiac rhythm management system (CRM) such as a pacemaker, defibrillator, cardiac resynchronizer, or the like. In another embodiment, the patient-internal device 510 may comprise, for example, an implantable transthoracic cardiac sensing and/or stimulation device (ITCS) as described in connection with FIG. 25 The patient-external device 520 may comprise an external breathing therapy device. For example, the external breathing therapy device may be a continuous positive airway pressure device (CPAP), bi-level positive airway pressure device (bi-PAP) or other positive airway pressure device, generically referred to herein as xPAP devices.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any device using forms of positive airway pressure (and negative pressure when necessary), whether continuous or otherwise.

An xPAP device 520 develops a positive air pressure that is delivered to the patient's airway through tubing 532 and mask 554 connected to the xPAP device 520. Positive airway pressure devices are often used to treat disordered breathing. In one configuration, for example, the positive airway pressure provided by the xPAP device 520 acts as a pneumatic splint keeping the patient's airway open and reducing the severity and/or number of occurrences of disordered breathing due to airway obstruction. In addition to delivering breathing therapy, the xPAP device 520 may provide a number of monitoring and/or diagnostic functions in relation to the respiratory system. For example, the xPAP device 520 may sense respiration using an oxygen sensor, a microphone, a flow meter, and/or other respiration sensing methods.

Components used in connection with acquiring and organizing sleep logbook information may be implemented by the patient-internal CRM 510 device, by the patient-external xPAP 520 device, or by both devices. Further, the CRM and the xPAP devices may be coupled to a remote computing device 560 such as a remote programmer and/or patient management server using wireless or wired link.

The CRM 510 may provide a first set of monitoring, diagnostic, and/or therapeutic functions to the patient. The xPAP device 520 may provide a second set of monitoring, diagnostic, and/or therapeutic functions to the patient. The CRM device 510, the xPAP device 520, or both may include sensors for sensing conditions associated with sleep such as those identified in Tables 1-2.

In one embodiment, sensors coupled to the CRM device 510 may sense a first set of conditions associated with sleep. The sensed information may be transmitted to sleep logbook circuitry incorporated in the xPAP device 520. Sensors coupled to the xPAP device 520 may sense a second set of conditions associated with sleep. The information sensed by the xPAP device and the CRM device may be organized by circuitry in the xPAP device into sleep logbook format.

In another embodiment, sensors coupled to the xPAP device 520 may sense a first set of information associated with sleep and transmit the information to the CRM device. Circuitry in the CRM device may combine the information acquired by the xPAP device sensors with information acquired by sensors coupled to the CRM device to generate the sleep logbook.

The sleep logbook system may be used in connection with the evaluation of sleep quality in accordance with various embodiments of the invention. The sleep logbook system illustrated in FIG. 2 may optionally include a sleep quality evaluation unit 234. The sleep quality evaluation unit 234 may use signals acquired from a variety of sources to evaluate data relevant to sleep quality. Further, the sleep quality evaluation unit 234 may include a circuitry for determining one or more metrics quantifying the patient's sleep quality.

The sleep logbook processor 232 may use the patient-internal and/or patient-external sensors 222 to detect physiological conditions relevant to sleep. The conditions detected using patient-internal sensors 210 may include, for example, heart rate, respiratory pattern, patient activity, and/or other conditions such as those listed in Tables 1-2 above. In one example configuration, whether the patient is snoring may be useful in evaluating sleep. Snoring data may be detected using an external microphone and acquired by the sleep logbook processor 232. In another configuration, ambient temperature and humidity may be factors related to the patient's sleep. The ambient temperature and humidity of the patient's room may be sensed using sensors located near patient. Signals from the temperature and humidity sensors may be transmitted to the sleep logbook processor 232. Limb and/or jaw movements may be sensed using patient-external accelerometers and/or other sensors placed in appropriate locations on or near the patient and transmitted to the sleep logbook processor.

Information relevant to sleep and/or sleep quality may also be reported by the patient. According to embodiments of the invention, the patient's self-described conditions, including medication use, tobacco use, perceptions of sleep quality, and/or psychological or emotional state, for example, may be relevant to sleep quality assessment. The patient may enter information about these conditions through an appropriate patient input device 223, such as a medical device programmer, coupled to the sleep logbook processor.

Some information related to sleep may be accessible through information systems 224, including network-based systems. For example, information about the patient's present cardiac, respiratory, or other therapy may be downloaded from an external device via a wireless or wired network. In another example, information about conditions affecting the patient, such as local air quality data, may be accessed through an internet-connected website.

The sleep logbook processor 232 may work cooperatively with one or more subsystems useful in implementing a sleep logbook system. The subsystems may include, for example a sleep detector 236 used to detect sleep onset, sleep offset, and arousal, for example. The sleep detector 236 may also detect sleep stages, including the various stages of NREM and REM sleep.

The sleep logbook processor 232 may include circuitry to detect various sleep-related disorders. For example, the sleep logbook processor 232 may include circuitry for detecting disordered breathing and circuitry for detecting abnormal nocturnal movements.

Collecting information related to sleep is enhanced by a reliable method for discriminating between a state of sleep and a state of wakefulness. One method of detecting sleep involves comparing one or more detected physiological conditions to thresholds indicative of sleep. When the detected conditions are consistent with thresholds indicating sleep, then sleep onset is declared. For example, decreased patient activity is a condition associated with sleep. When the patient's activity falls below a predetermined threshold, the system declares the onset of sleep. When the patient's activity rises above the threshold, the system declares the end of sleep. In a similar manner, a number of patient conditions, such as heart rate, respiration rate, brain wave activity, etc., may be compared individually or collectively compared to thresholds or other indices to detect sleep.

Methods and systems for detecting sleep are described in commonly owned U.S. patent application Ser. No. 10/309,771, filed Dec. 4, 2002, now U.S. Pat. No. 7,189,204, which is incorporated herein by reference. The method involves adjusting a sleep threshold associated with a first patient condition using a second patient condition. The first patient condition is compared to the adjusted threshold to determine if the patient is asleep or awake.

Figure 6:
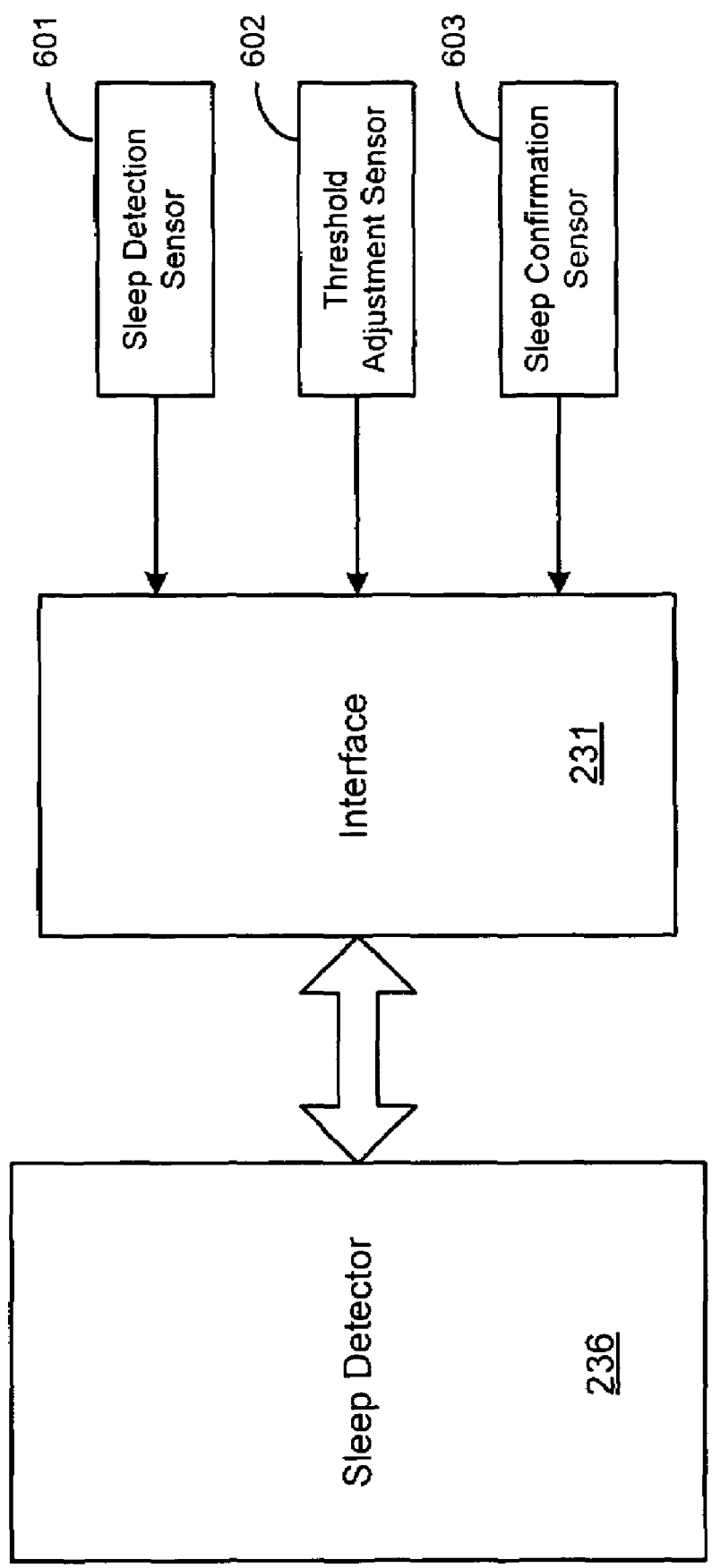
FIG. 6 illustrates sleep detection circuitry that may be used in connection with a sleep logbook in accordance with embodiments of the invention.

FIG. 6 illustrates a portion of the sleep logbook circuitry illustrated in FIG. 2 that may be used for sleep detection. The sleep detector 236 uses a number of sensors 601, 602, 603 to sense sleep-related patient conditions. A representative set of sleep-related conditions include, for example, patient activity, patient location, posture, heart rate, QT interval, eye movement, respiration rate, transthoracic impedance, tidal volume, minute ventilation, brain activity, muscle tone, body temperature, time of day, and blood oxygen level.

According to embodiments of the invention, a first sleep-related condition detected using a sleep detection sensor 601 is compared to a sleep threshold for detecting the onset and termination of sleep. A second sleep-related condition, detected using a threshold adjustment sensor 602, is used to adjust the sleep threshold. Although the example described herein involves one sleep detection sensor 601 and one threshold adjustment sensor 602, any number of thresholds or other indices corresponding to a number of sleep detection sensors may be used. Furthermore, conditions detected using any number of adjustment sensors may be used to adjust the thresholds or indices of a plurality of sleep detection signals. Additional sleep-related signals derived from one or more confirmation sensors 603 may optionally be used to confirm the onset or termination of the sleep condition.

Signals derived from the sensors 601, 602, 603 are received by interface circuitry 231 that may include, for example, amplifiers, signal processing circuitry, and/or A/D conversion circuitry for processing each sensor signal. The interface circuitry 231 may further include sensor drive circuitry required to activate the sensors 601, 602, 603.

The sleep detector 236 is configured to compare the level of a first sleep-related condition detected using the sleep detection sensor 601 to a sleep threshold adjusted by a second sleep-related condition detected using the threshold adjustment sensor 602. A determination of sleep onset or sleep termination may be made by the sleep detector 236 based on the comparison. The onset or termination of sleep may optionally be confirmed using patient conditions derived using a sleep confirmation sensor 603.

Figure 7:
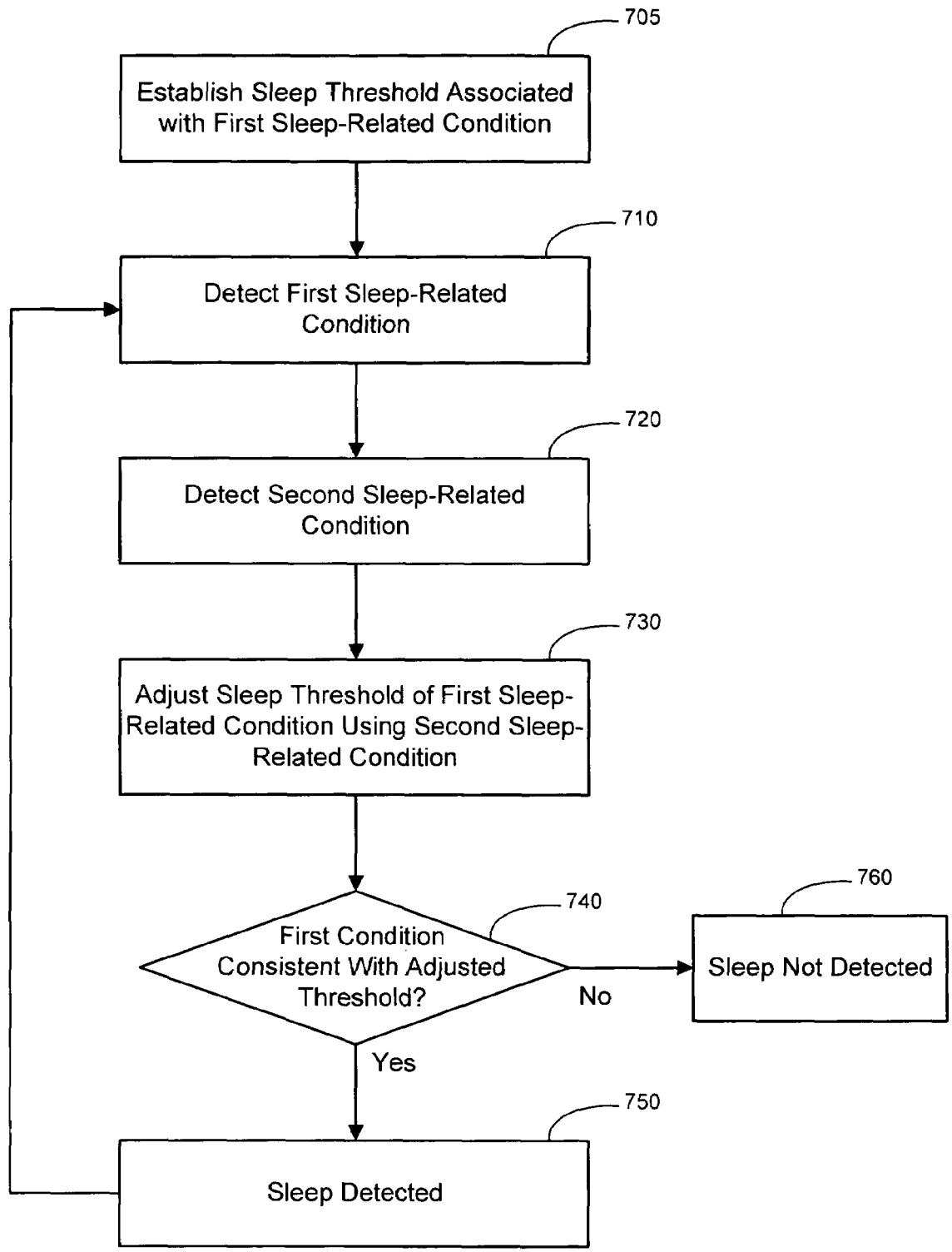
FIGS. 7 and 8 are flowcharts illustrating methods of sleep detection that may be implemented in a sleep logbook system in accordance with embodiments of the invention.

FIG. 7 is a flow chart illustrating a method of detecting sleep used in a sleep logbook system configured according to embodiments of the invention. A sleep threshold associated with a first sleep-related patient condition is established 705. The sleep threshold may be determined from clinical data of a sleep threshold acquired using a group of subjects, for example. The sleep threshold may also be determined using historical data taken from the particular patient for whom the sleep condition is to be detected.

First and second sleep-related conditions are detected 710, 720. The first and the second sleep-related conditions may be detected using sensors implanted in the patient, attached externally to the patient or located remote from the patient, for example, as previously described in connection with FIG. 3. The first and the second sleep-related conditions may include any condition associated with sleep and are not limited to the representative sleep-related conditions listed above.

The sleep threshold established for the first sleep-related condition is adjusted using the second sleep-related condition 730. For example, if the second sleep-related condition indicates a high level of activity that is incompatible with a sleep state, the sleep threshold of the first sleep-related condition may be adjusted downward to require sensing a decreased level of the first sleep-related condition before a sleep condition is detected.

If the first sleep-related condition is consistent with sleep according to the adjusted sleep threshold. 740, sleep is detected 750. If the first sleep-related condition is not consistent with sleep using the adjusted sleep threshold sleep is not detected 760. After either sleep is detected or not detected, the first and the second sleep-related conditions continue to be detected 710, 720 and the threshold adjusted 730 allowing further evaluation of the sleep state.

Figure 8:
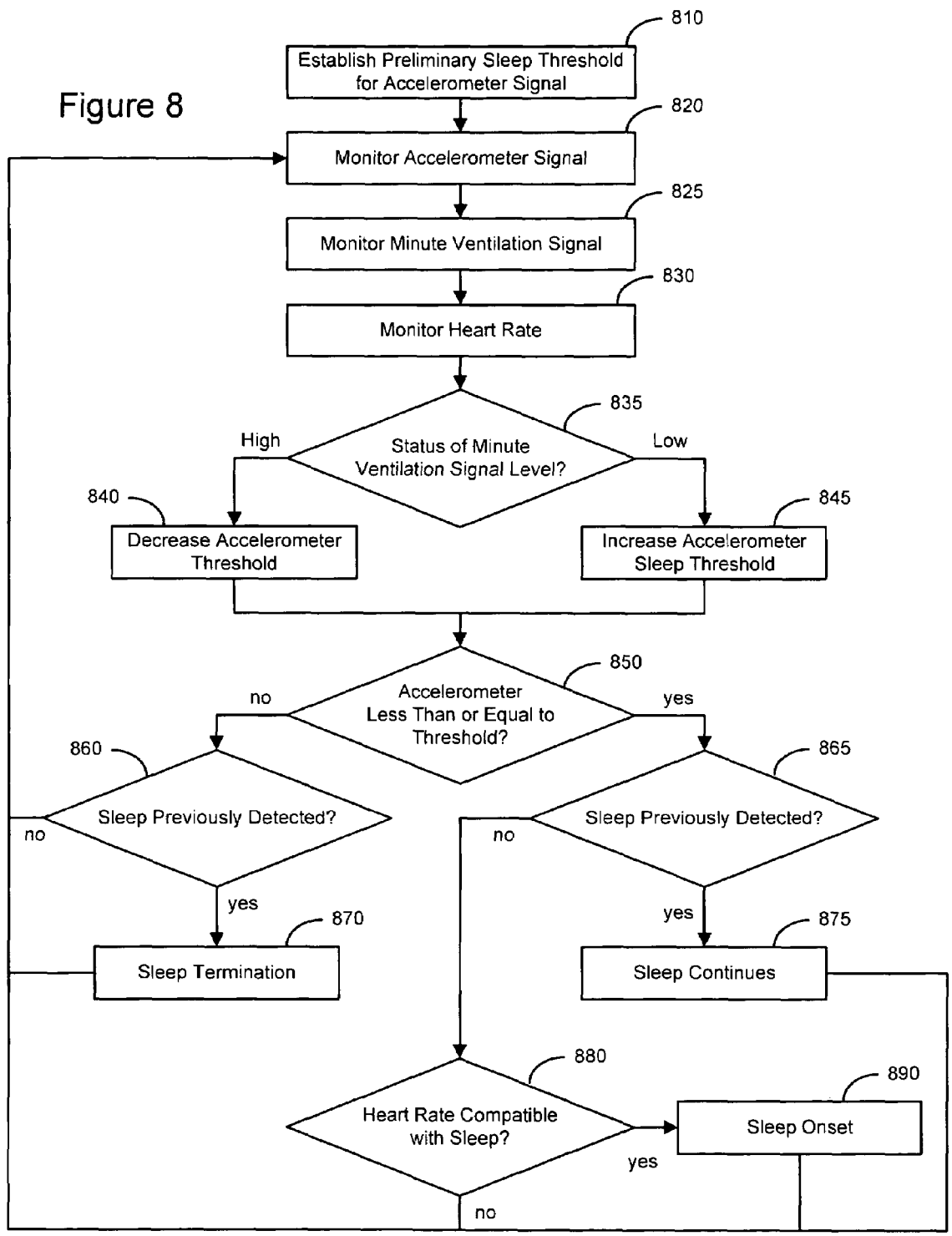

The flow chart of FIG. 8 illustrates a method for detecting sleep using accelerometer and minute ventilation (MV) signals according to embodiments of the invention. In the method illustrated in FIG. 8, an accelerometer and a minute ventilation sensor are used to detect patient activity and patient respiration conditions, respectively. A preliminary sleep threshold is determined 810 with respect to the patient activity condition sensed by the accelerometer. The preliminary sleep threshold may be determined from clinical data derived from a group of subjects or from historical data taken from the patient over a period of time.

The activity condition of the patient is monitored 820 using an accelerometer that may be incorporated in an implantable cardiac rhythm management system as described in connection with FIG. 2. Alternatively, the accelerometer may be attached externally to the patient. The patient's MV condition is monitored 825, for example, using a transthoracic impedance sensor. A transthoracic impedance sensor may be implemented as a component of an implantable CRM device.

In this embodiment, the patient's activity represents the sleep detection condition and is compared to the-sleep threshold. The patient's MV is used as the threshold adjustment condition to adjust the sleep threshold. In addition, in this example, the patient's heart rate is monitored 830 and used to provide a sleep confirmation condition.

The sleep threshold adjustment is accomplished using the patient's MV condition to adjust the activity sleep threshold. If the patient's MV condition is low relative to an expected MV level associated with sleep, the activity sleep threshold is increased. Similarly, if the patient's MV level is high relative to an expected MV level associated with sleep, the activity sleep threshold is decreased. Thus, when the patient's MV level is high, less activity is required to make the determination that the patient is sleeping. Conversely when the patient's MV level is relatively low, a higher activity level may result in detection of sleep. The use of two sleep-related conditions to determine the patient's sleep state enhances the accuracy of sleep detection over previous methods.

Various signal processing techniques may be employed to process the raw sensor signals. For example, a moving average of a plurality of samples of the sensor signals may be calculated. Furthermore, the sensor signals may be amplified, filtered, digitized or otherwise processed.

If the MV level is high 835 relative to an expected MV level associated with sleep, the activity sleep threshold is decreased 840. If the MV level is low 835 relative to an expected MV level associated with sleep, the activity sleep threshold is increased 845.

If the patient's activity level is less than or equal to the adjusted sleep threshold 850, and if the patient is currently not in a sleep state 865, then the patient's heart rate is checked 880 to confirm that the patient is asleep. If the patient's heart rate is compatible with sleep 880, then sleep onset is determined 890. If the patient's heart rate is incompatible with sleep, then the patient's sleep-related conditions continue to be monitored.

If the patient's activity level is less than or equal to the adjusted sleep threshold 850 and if the patient is currently in a sleep state 865, then a continuing sleep state is determined 875 and the patient's sleep-related conditions continue to be monitored for sleep termination to occur.

If the patient's activity level is greater than the adjusted sleep threshold 850 and the patient is not currently in a sleep state 860, then the patient's sleep-related conditions continue to be monitored until sleep onset is detected 890. If the activity level is greater than the adjusted sleep threshold 850 and the patient is currently in a sleep state 860, then sleep termination is detected 870.

Figure 9:
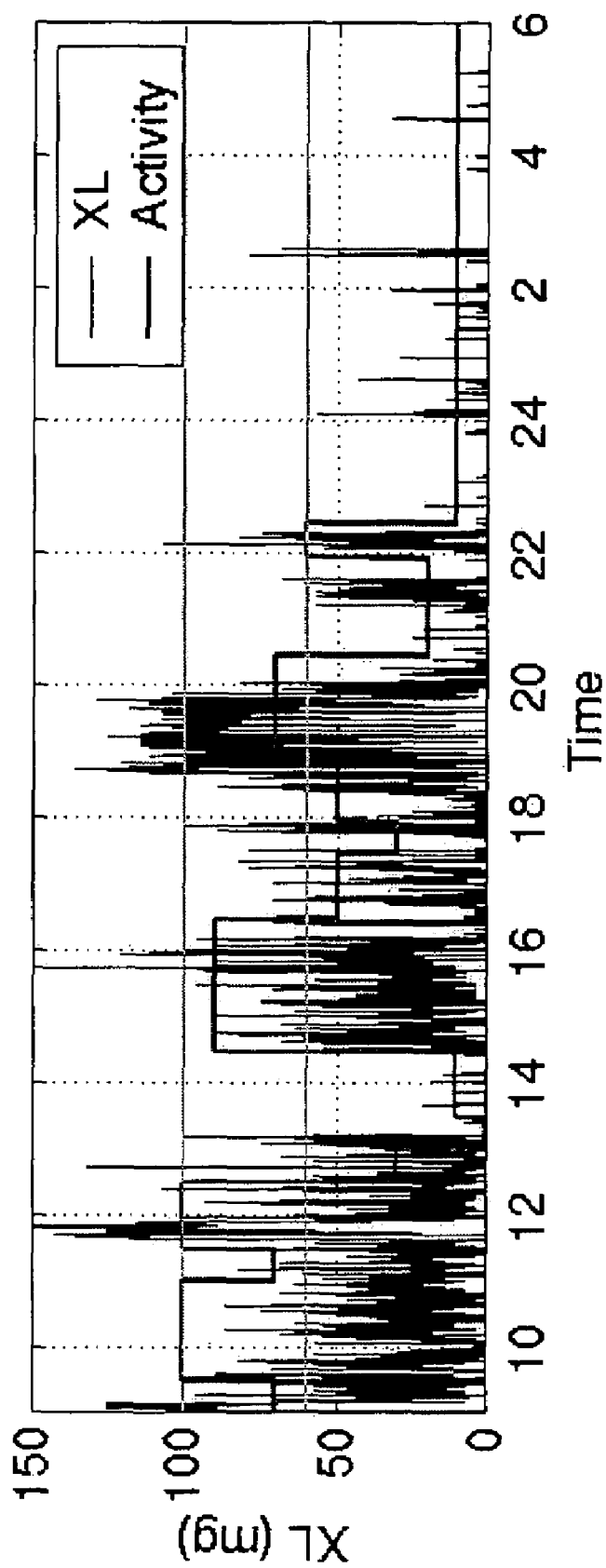
FIGS. 9 and 10 are graphs illustrating patient's activity and heart rate, respectively.
Figure 10:
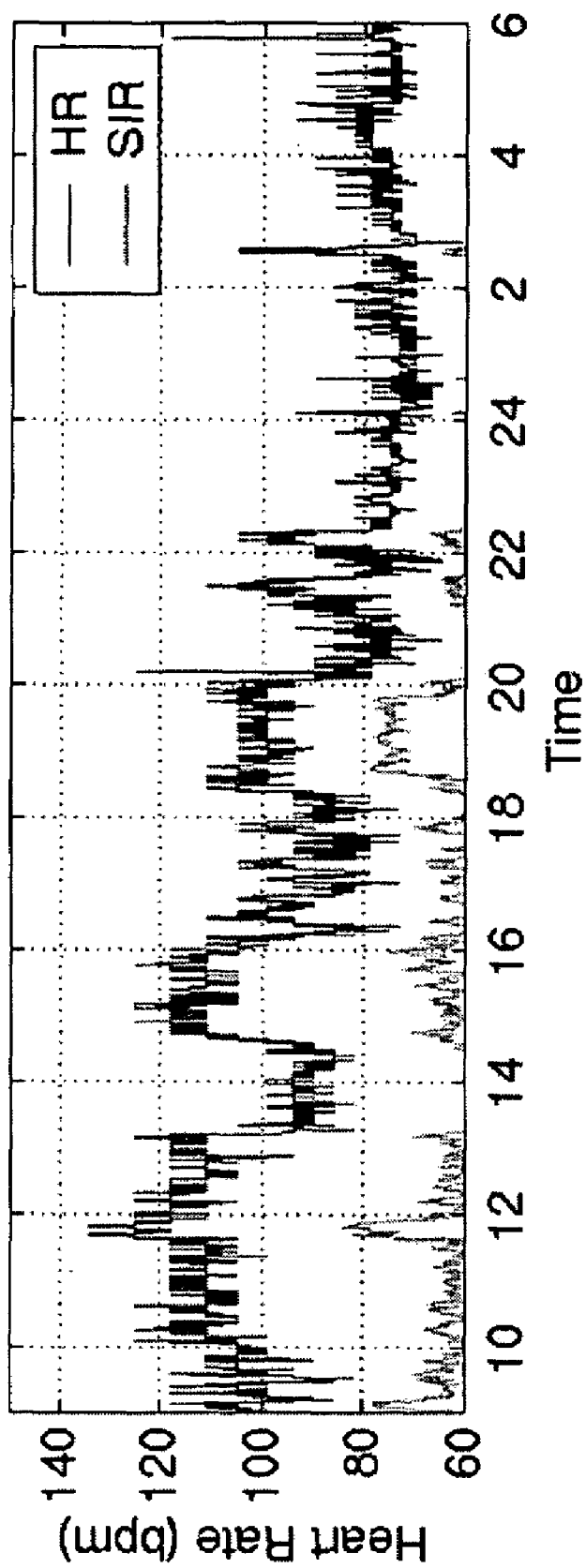

The graphs of FIGS. 9-12 illustrate the adjustment of the activity sleep threshold. The relationship between patient activity and the accelerometer and MV signals is trended over a period of time to determine relative signal levels associated with sleep. The graph of FIG. 9 illustrates the patient's activity as indicated by an accelerometer. The patient's heart rate (HR) and sensor indicated heart rate (SIR) for the same period are shown in the graph of FIG. 10. The accelerometer signal indicates a period of sleep associated with a relatively low level of activity beginning slightly before 23:00 and continuing through 6:00. The patient's heart rate appropriately tracks the activity level indicated by the accelerometer indicating a similar period of decreased heart rate corresponding to sleep. The signal level of the accelerometer during known periods of sleep may be used to establish a threshold for sleep detection.

Figure 11:
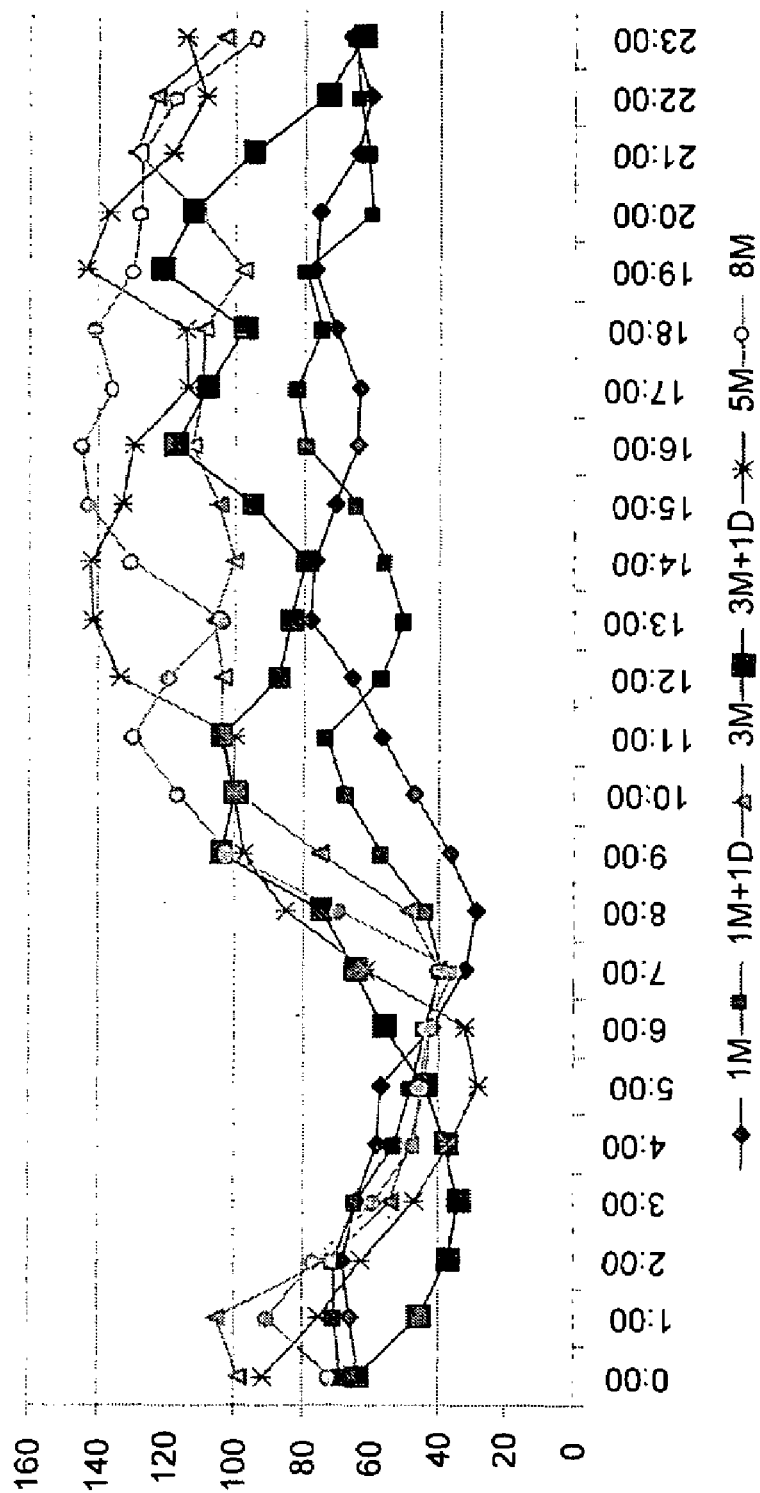
FIG. 11 is a graph of a patient's minute ventilation signal over time.

FIG. 11 is a graph of the patient's minute ventilation signal over time. Historical data of averaged minute ventilation is graphed to indicate variations over a 24 hour period. MV data is shown for averages of 1 month to 8 months. The minute ventilation data may be used to determine the minute ventilation signal level associated with sleep. In this example, a composite minute ventilation graph using the historical data presents a roughly sinusoidal shape with the relatively low minute ventilation levels occurring during the period approximately from hours 21:00 through 8:00. The decreased minute ventilation level is associated with periods of sleep. The minute ventilation level associated with sleep is used to implement sleep threshold adjustment.

Figure 12:
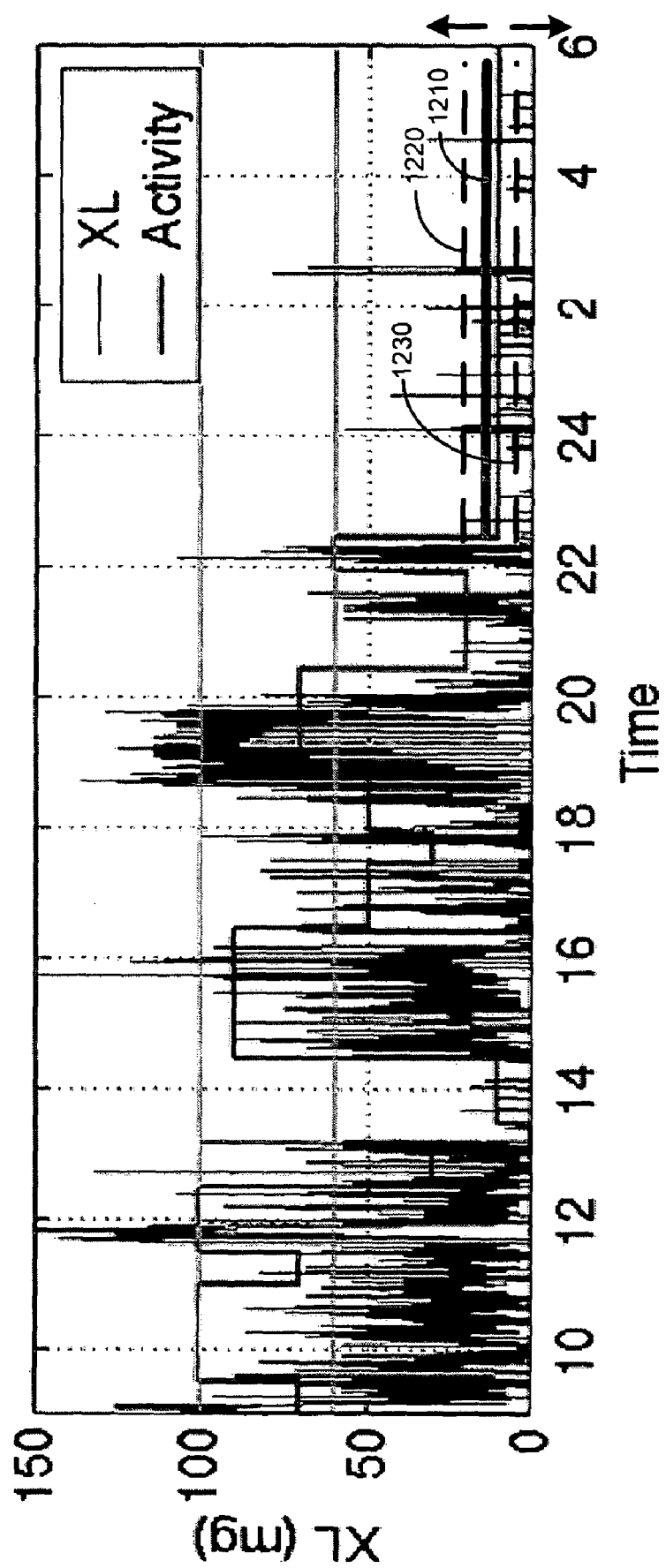
FIG. 12 illustrates adjustment of the activity sleep threshold using the MV data in accordance with embodiments of the invention.

FIG. 12 illustrates adjustment of the activity sleep threshold using the MV data. The initial sleep threshold 1210 is established using the baseline activity data acquired as discussed above. If the patient's MV level is low relative to an expected MV level associated with sleep, the activity sleep threshold is increased 1220. If the patient's MV level is high relative to an expected MV level associated with sleep, the activity sleep threshold is decreased 1230. When the patient's MV level is high, less activity detected by the accelerometer is required to make the determination that the patient is sleeping. However, if the patient's MV level is relatively low, a higher activity level may result in detection of sleep. The use of two sleep-related signals to establish and adjust a sleep threshold enhances the accuracy of sleep detection over previous methods.

Additional sleep-related conditions may be sensed and used to improve the sleep detection method described above. For example, a posture sensor may be used to detect the posture of the patient and used to confirm sleep. If the posture sensor signal indicates an upright posture, then the posture sensor signal may be used to override a determination of sleep using the sleep detection and threshold adjustment conditions. Other conditions may also be used in connection with sleep determination or confirmation, including the representative set of sleep-related conditions indicated above. In another example, a proximity to bed sensor may be used alone or in combination with a posture sensor to detect that the patient is in bed and is lying down.

A sleep detection system may detect sleep onset, termination, arousals as well as the sleep stages, including REM and non-REM sleep. REM sleep may be discriminated from NREM sleep, for example, by examining one or more signals indicative of REM, e.g., muscle atonia, rapid eye movements, or EEG signals. Methods and systems for detecting REM sleep that are particularly useful for patients with implantable devices are discussed in commonly owned U.S. patent application Ser. No. 10/643,006, filed on Aug. 18, 2003, now U.S. Publication No. 2005/0043652, and incorporated herein by reference. Various conditions indicative of sleep state may be detected using sensors, e.g., electroencephalogram (EEG), electrooculogram (EOG), or electromyogram (EMG) sensors, coupled through wired or wireless connections to the sleep detection circuitry. The sleep detection circuitry may analyze the various patient conditions sensed by the sensors to track the patient's sleep through various sleep states, including REM and NREM stages.

Disordered breathing is a fairly common sleep disorder that affects a significant percentage of patients between 30 and 60 years. Sleep disordered breathing is associated with excessive daytime sleepiness, systemic hypertension, increased risk of stroke, angina and myocardial infarction. Disturbed respiration can be particularly serious for patients concurrently suffering from cardiovascular deficiencies. Disordered breathing is particularly prevalent among congestive heart failure patients, and may contribute to the progression of heart failure.

Various movement disorders, such as restless leg syndrome (RLS), periodic limb-movement disorder (PLMD), and/or bruxism, may also interfere with sleep quality. Movement disorders such as restless leg syndrome (RLS), and the related condition, periodic limb movement disorder (PLMD), are emerging as one of the more common sleep disorders, especially among older patients. Restless leg syndrome is a disorder causing unpleasant crawling, prickling, or tingling sensations in the legs and feet and an urge to move them for relief. RLS leads to constant leg movement during the day and insomnia or fragmented sleep at night. Severe RLS is most common in elderly people, although symptoms may develop at any age. In some cases, it may be linked to other conditions such as anemia, pregnancy, or diabetes. Periodic limb movement disorder (PLMD), a disorder that causes repetitive jerking movements of the limbs, especially the legs. These movements occur approximately every 20 to 40 seconds and cause repeated arousals and severely fragmented sleep.

Figure 13:
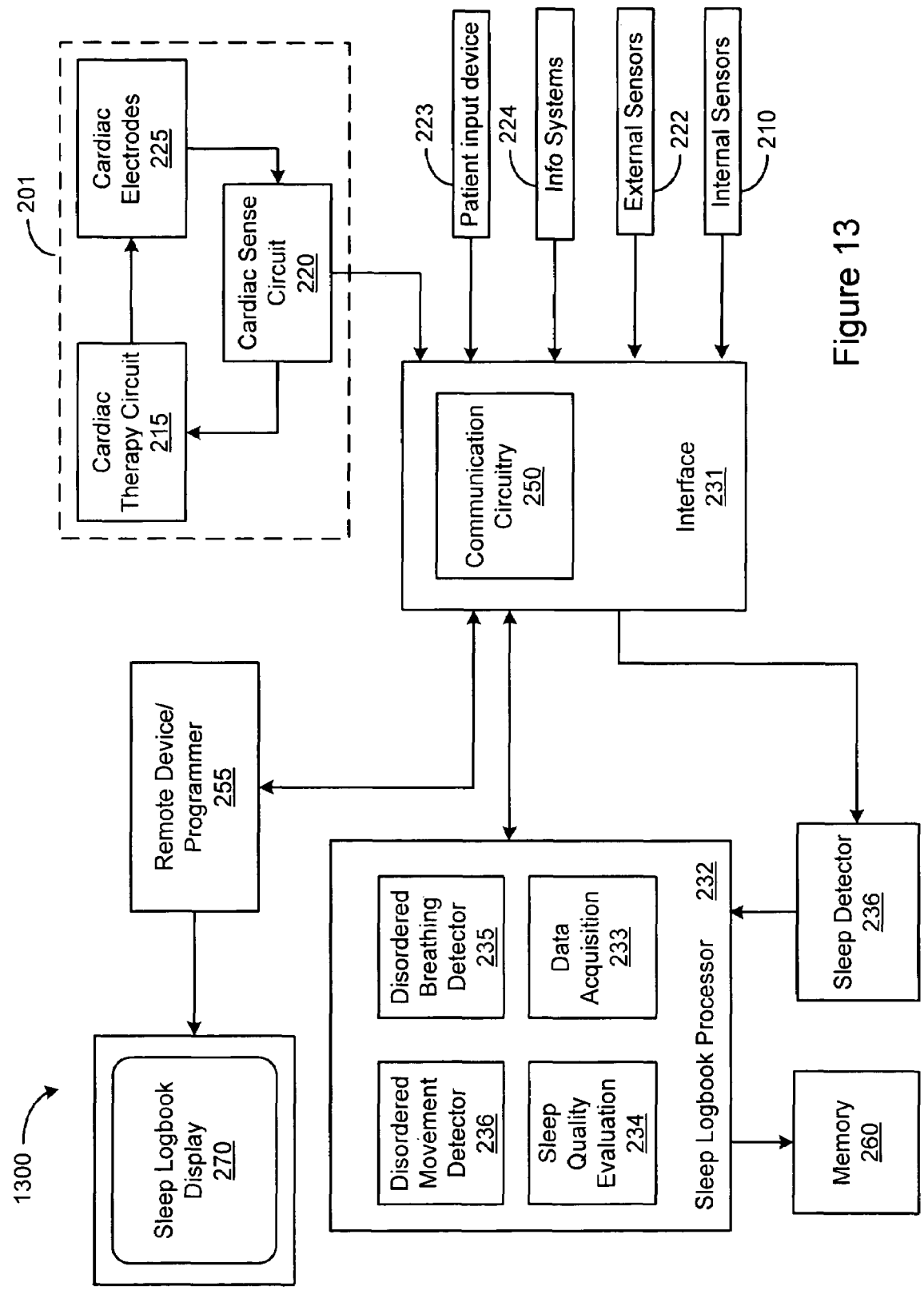
FIG. 13 is a block diagram of a sleep logbook system including disordered breathing and disordered movement detectors in accordance with embodiments of the invention.

FIG. 13 illustrates a block diagram of a medical system similar to that discussed in connection with FIG. 2 above. The medical system of FIG. 13 includes disordered breathing detection circuitry 235 to detect episodes of disordered breathing and movement disorder detection circuitry 236 to detect movement disorder episodes.

For example, the movement disorder detection circuitry 236 may be used to evaluate the movements of a patient during the night to detect nocturnal movement disorders such as RLS, PLMD, and/or bruxism. The patient may be instrumented with accelerometers located on the limbs or jaw, for example, to sense patient movement. Excessive movement, or movements having a characteristic pattern, e.g., periodic limb or jaw movements, may be classified as abnormal nocturnal movements. For example, bruxism is a sleep disorder wherein the patient grinds his teeth during sleep. An accelerometer attached to the patient's jaw may be used to sense movement of the jaw. Signals from the jaw accelerometer may be transferred to the abnormal movement detector for evaluation to determine if the movements are excessive or unusually periodic, indicating bruxism. In a similar implementation, accelerometers attached to the patient's limbs may generate signals used by the abnormal movement detector 236 to detect and classify disorders such as RLS and PLMD.

Disordered breathing may be detected in numerous ways using one or more of the patient conditions, such as those listed in Table 1. Methods and systems for detecting disordered breathing, aspects of which may be incorporated into a sleep logbook system of the present invention, are described in commonly owned U.S. patent application Ser. No. 10/309, 770, filed Dec. 4, 2002, now U.S. Pat. No. 7,252,640, which is incorporated herein by reference. According to this approach, disordered breathing may be detected by examining characteristics of the patient's respiration patterns to determine if the respiration patterns are consistent with disordered breathing.

Figure 14:
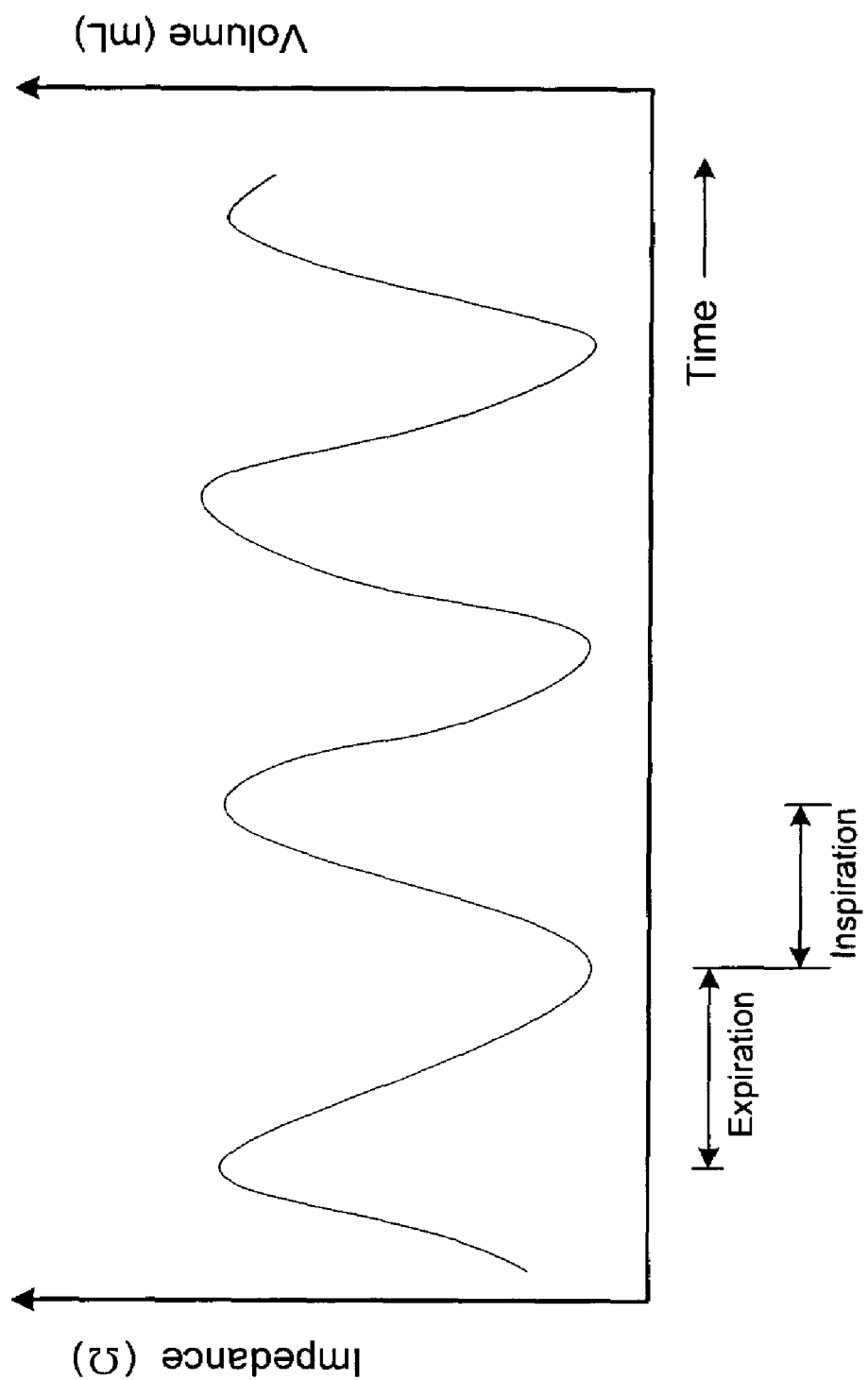
FIG. 14 illustrates a normal respiration pattern as represented by a transthoracic impedance sensor signal.

FIG. 14 illustrates a normal respiration pattern as represented by a transthoracic impedance sensor signal. The transthoracic impedance increases during respiratory inspiration and decreases during respiratory expiration. During NREM sleep, a normal respiration pattern includes regular, rhythmic inspiration-expiration cycles without substantial interruptions.

Figure 15:
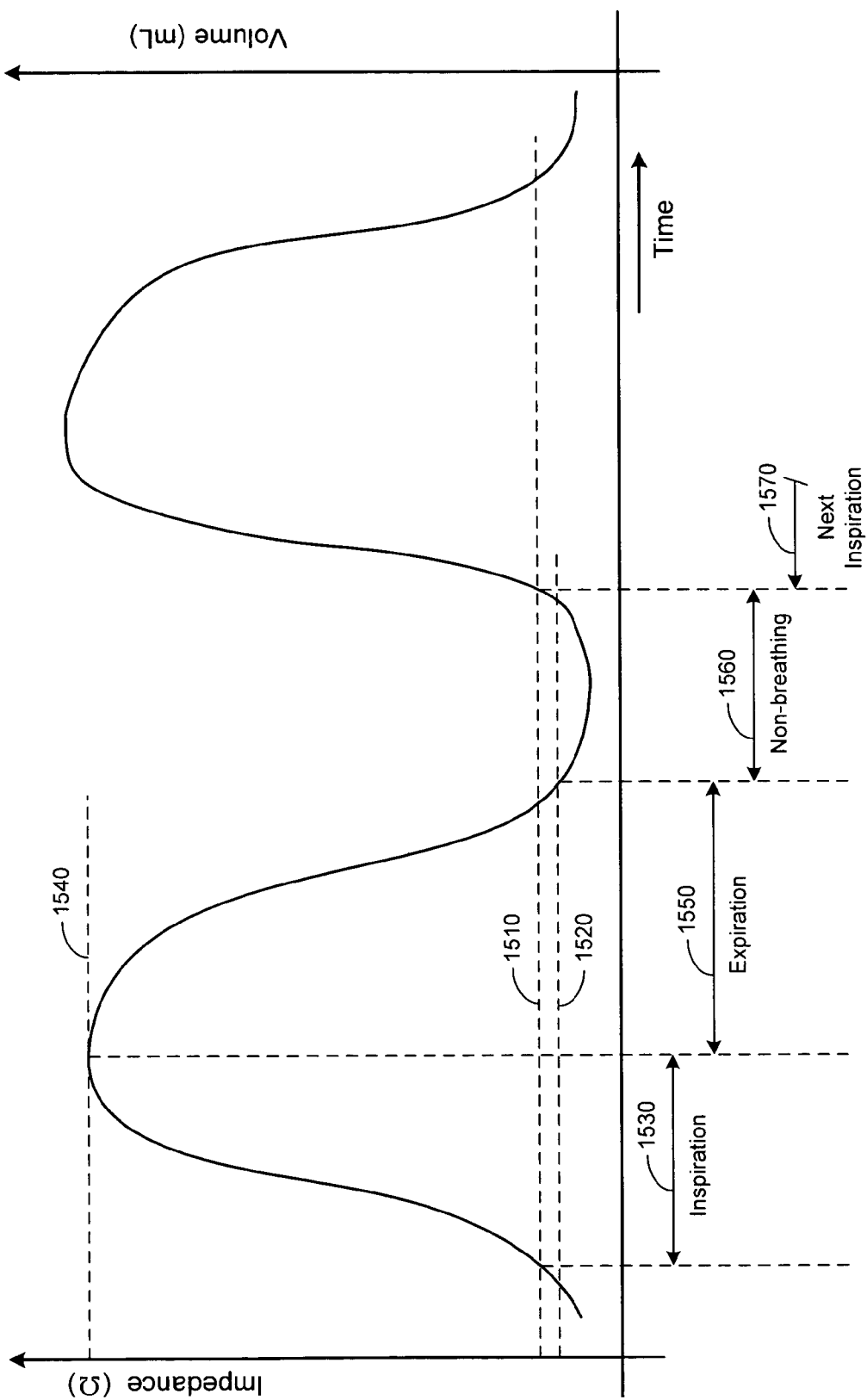
FIG. 15 illustrates respiration intervals used for disordered breathing detection according to an embodiment of the invention.

In one embodiment, detection of disordered breathing, including, for example, sleep apnea and hypopnea, involves defining and examining a number of respiratory cycle intervals. FIG. 15 illustrates respiration intervals used for disordered breathing detection according to an embodiment of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1510 and expiration 1520 thresholds. The inspiration threshold 1510 marks the beginning of an inspiration period 1530 and is determined by the transthoracic impedance signal rising above the inspiration threshold 1510. The inspiration period 1530 ends when the transthoracic impedance signal is maximum 1540. A maximum transthoracic impedance signal 1540 corresponds to both the end of the inspiration interval 1530 and the beginning of the expiration interval 1550. The expiration interval 1550 continues until the transthoracic impedance falls below an expiration threshold 1520. A non-breathing interval 1560 starts from the end of the expiration period 1550 and continues until the beginning of the next inspiration period 1570.

Figure 16:
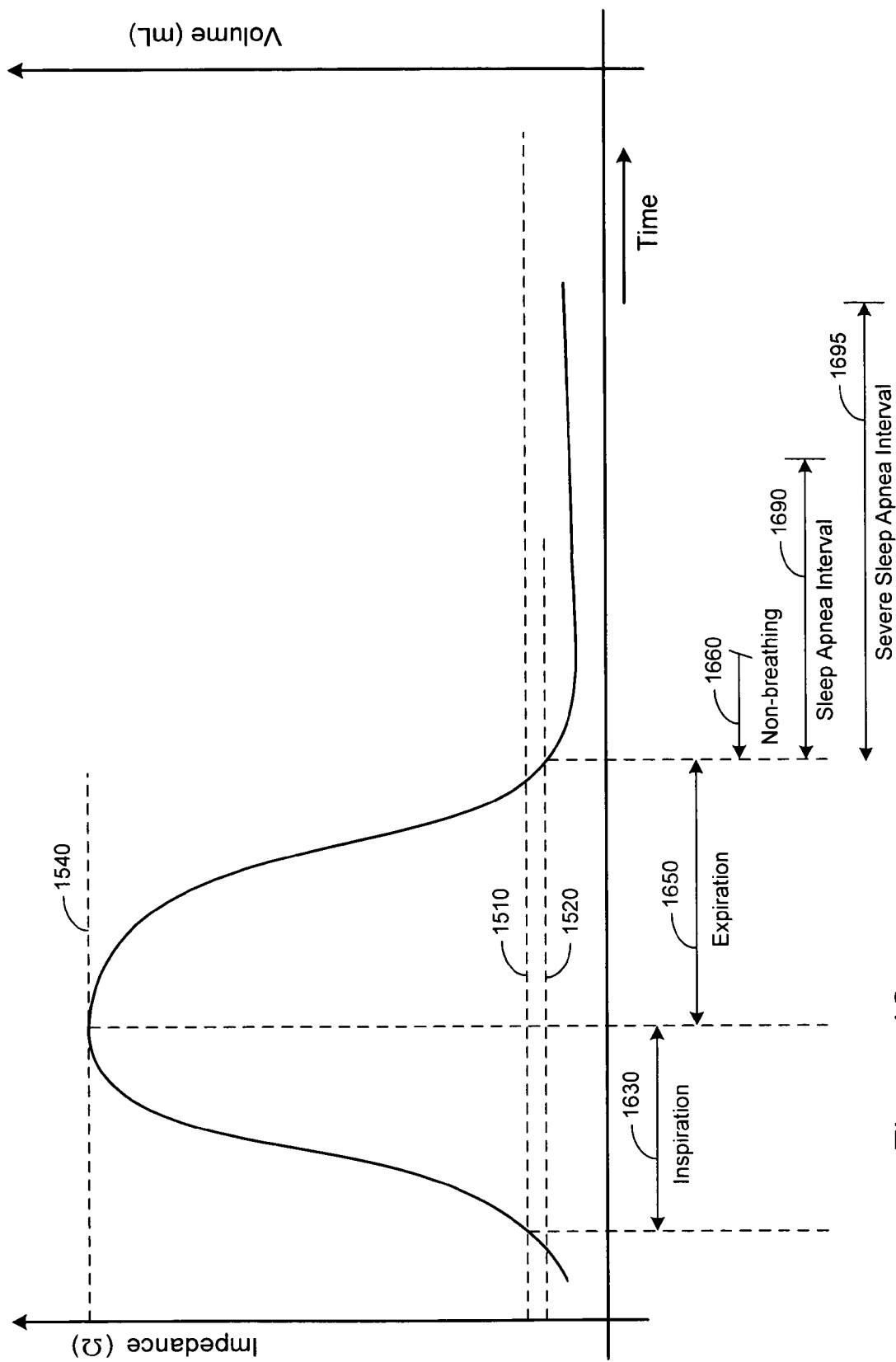
FIG. 16 illustrates detection of sleep apnea and severe sleep apnea according to embodiments of the invention.

Detection of sleep apnea and severe sleep apnea according to embodiments of the invention are illustrated in FIG. 16. The patient's respiration signals are monitored and the respiration cycles are defined according to inspiration 1630, expiration 1650, and non-breathing 1660 intervals as described in connection with FIG. 15. A condition of sleep apnea is detected when a non-breathing period 1660 exceeds a first predetermined interval 1690, denoted the sleep apnea interval. A condition of severe sleep apnea is detected when the non-breathing period 1660 exceeds a second predetermined interval 1695, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of disordered breathing characterized by abnormally shallow breathing. FIGS. 17A-B are graphs of respiration patterns derived from transthoracic impedance measurements. The graphs compare the tidal volume of a normal breathing cycle to the tidal volume of a hypopnea episode. FIG. 17A illustrates normal respiration tidal volume and rate. As shown in FIG. 17B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle may be derived from transthoracic impedance measurements. The hypopnea tidal volume threshold may be established using clinical results providing a representative tidal volume and duration for hypopnea events. In one configuration, hypopnea is detected when an average of the patient's respiratory tidal volume taken over a selected time interval falls below the hypopnea tidal volume threshold.

Figure 18:
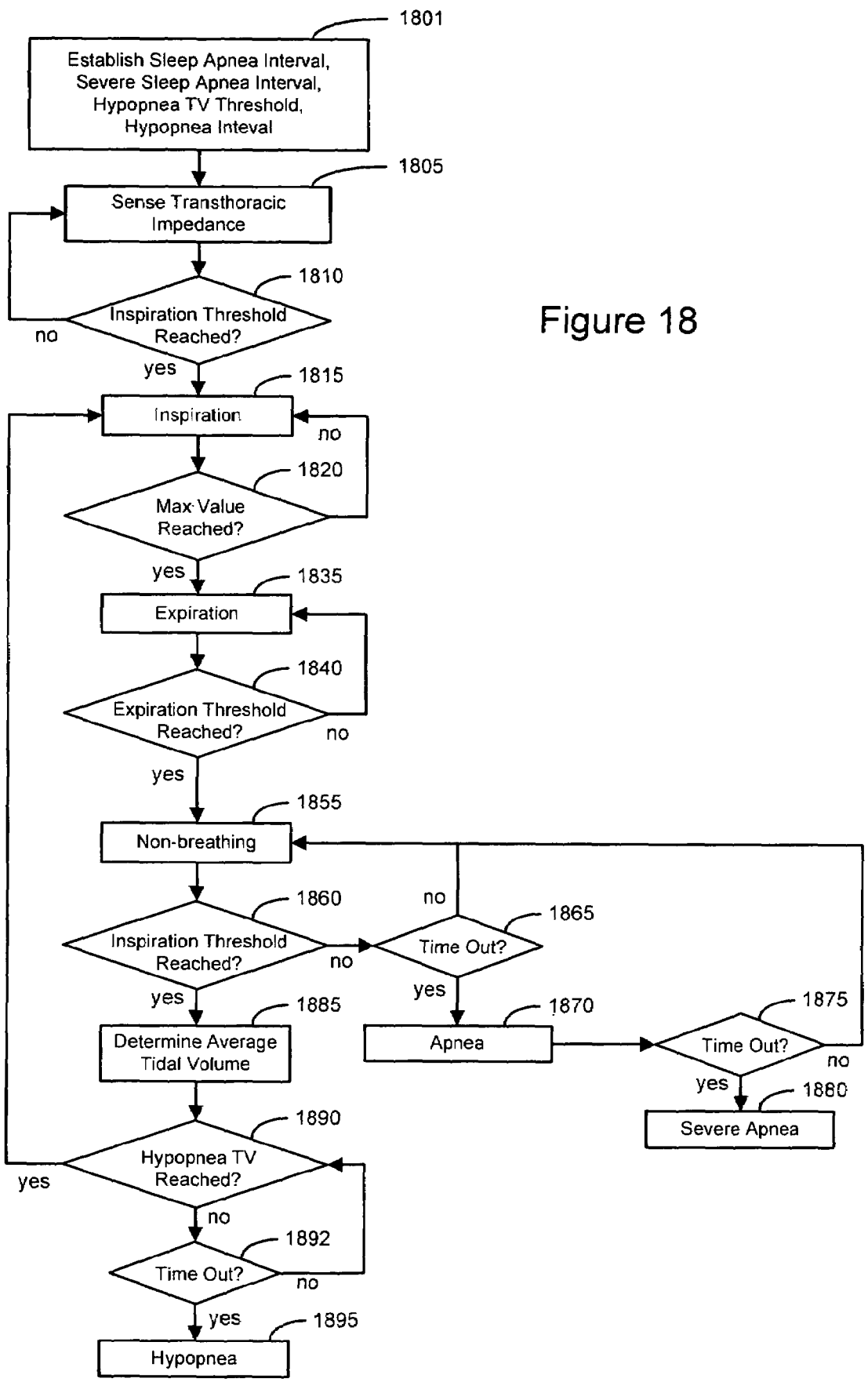
FIG. 18 is a flowchart illustrating a method of apnea and/or hypopnea detection according to embodiments of the invention.

FIG. 18 is a flowchart illustrating a method of apnea and/or hypopnea detection according to embodiments of the invention. Various parameters are established 1801 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is detected 1805. If the transthoracic impedance exceeds 1810 the inspiration threshold, the beginning of an inspiration interval is detected 1815. If the transthoracic impedance remains below 1810 the inspiration threshold, then the impedance signal is checked 1805 periodically until inspiration 1815 occurs.

During the inspiration interval, the patient's transthoracic impedance is monitored until a maximum value of the transthoracic impedance is detected 1820. Detection of the maximum value signals an end of the inspiration period and a beginning of an expiration period 1835.

The expiration interval is characterized by decreasing transthoracic impedance. When the transthoracic impedance falls below 1840 the expiration threshold, a non-breathing interval is detected 1855.

If the transthoracic impedance does not exceed 1860 the inspiration threshold within a first predetermined interval 1865, denoted the sleep apnea interval, then a condition of sleep apnea is detected 1870. Severe sleep apnea is detected 1880 if the non-breathing period extends beyond a second predetermined interval 1875, denoted the severe sleep apnea interval.

When the transthoracic impedance exceeds 1860 the inspiration threshold, the tidal volume from the peak-to-peak transthoracic impedance is calculated 1885. The peak-to-peak transthoracic impedance provides a value proportional to the tidal volume of the respiration cycle. This value is compared 1890 to a hypopnea tidal volume threshold. If the peak-to-peak transthoracic impedance is consistent with 1890 the hypopnea tidal volume threshold for a predetermined time 1892, then a hypopnea cycle is detected 1895.

Additional sensors, such as motion sensors and/or posture sensors, may be used to confirm or verify the detection of a sleep apnea or hypopnea episode. The additional sensors may be employed to prevent false or missed detections of sleep apnea or hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern may be determined to represent a disordered breathing episode based on the comparison.

Figure 19:
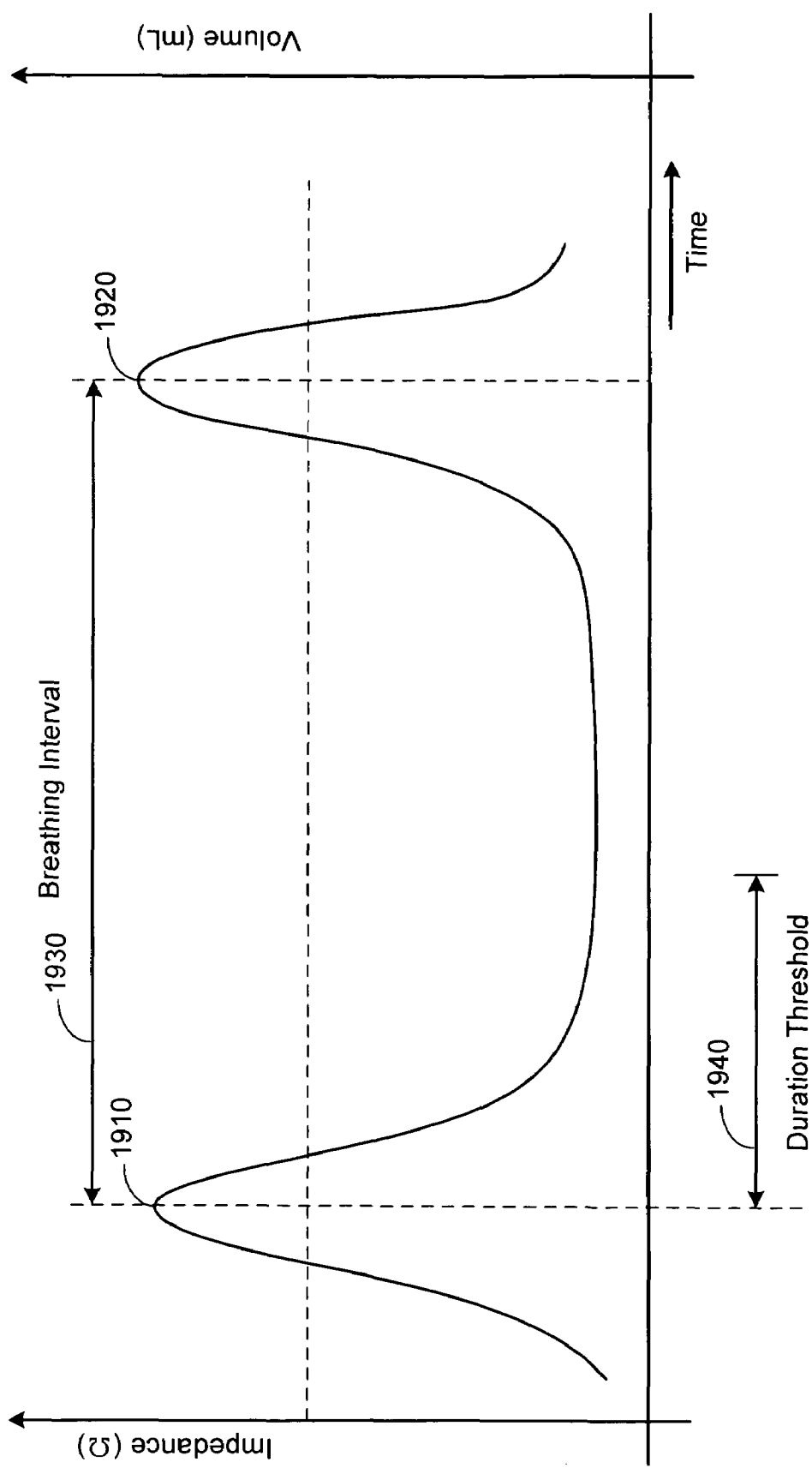
FIG. 19 is a graph illustrating breathing intervals that may be used in connection with disordered breathing detection in accordance with embodiments of the invention.

According to this embodiment, a breath interval is established for each respiration cycle. A breath interval represents the interval of time between successive breaths, as illustrated in FIG. 19. A breath interval 1930 may be defined in a variety of ways, for example, as the interval of time between successive maxima 1910,1920 of the impedance signal waveform.

Detection of disordered breathing, in accordance with methods of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 19. Apnea represents a period of non-breathing. A breath interval 1930 exceeding a duration threshold 1940 comprises an apnea episode.

Hypopnea may be detected using a duration threshold and a tidal volume threshold. A hypopnea event represents a period of shallow breathing greater than the duration threshold. Each respiration cycle in a hypopnea event is characterized by a tidal volume less than the tidal volume threshold. Further, the decreased tidal volume cycles persist longer than the duration threshold.

Figure 20:
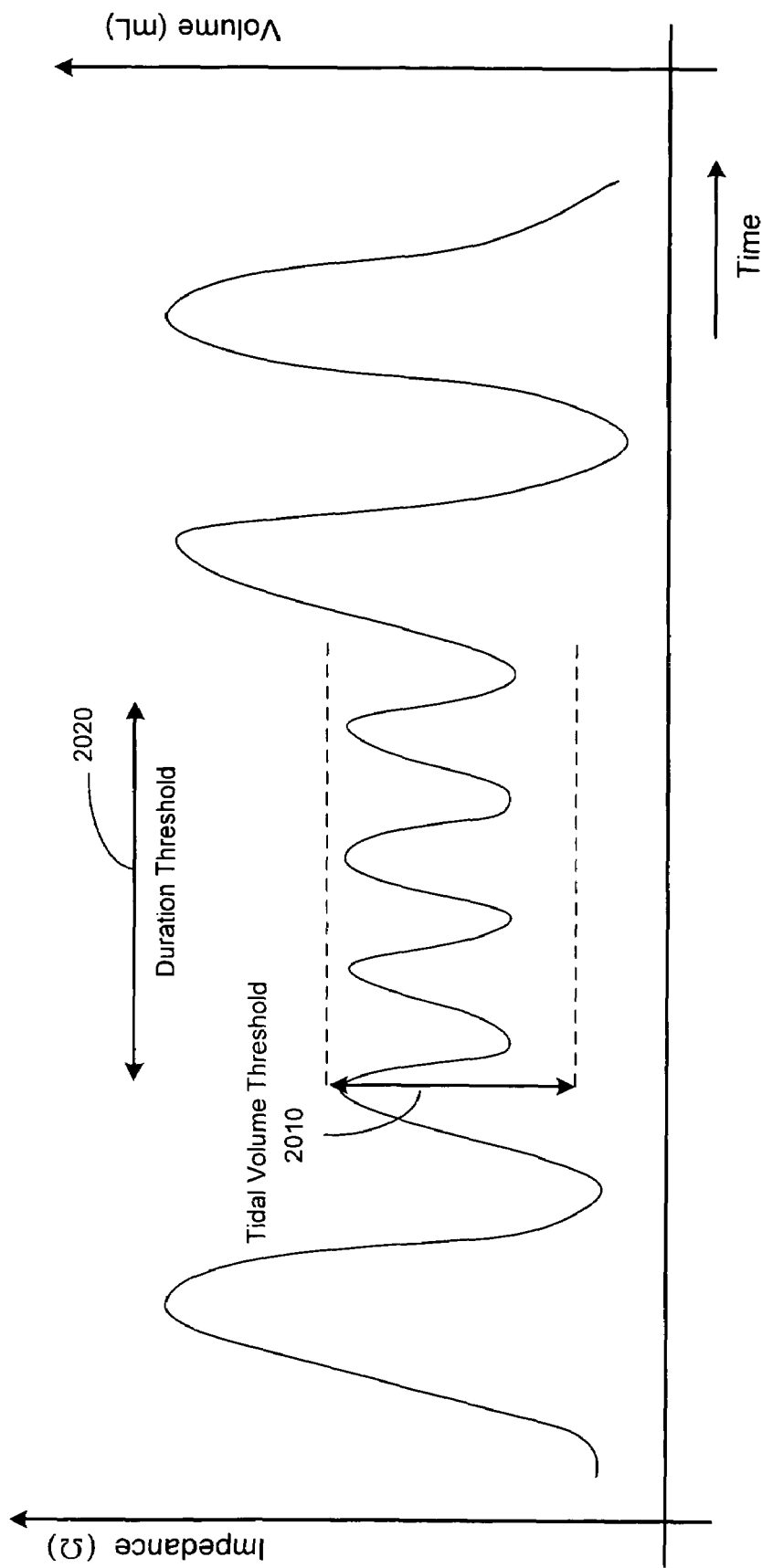
FIG. 20 illustrates a hypopnea detection approach in accordance with embodiments of the invention.

A hypopnea detection approach, in accordance with embodiments of the invention, is illustrated in FIG. 20. Shallow breathing is detected when the tidal volume of one or more breaths is below a tidal volume threshold 2010. If the shallow breathing continues for an interval greater than a duration threshold 2020, then the breathing pattern represented by the sequence of shallow respiration cycles, is classified as a hypopnea event.

Figure 21A:
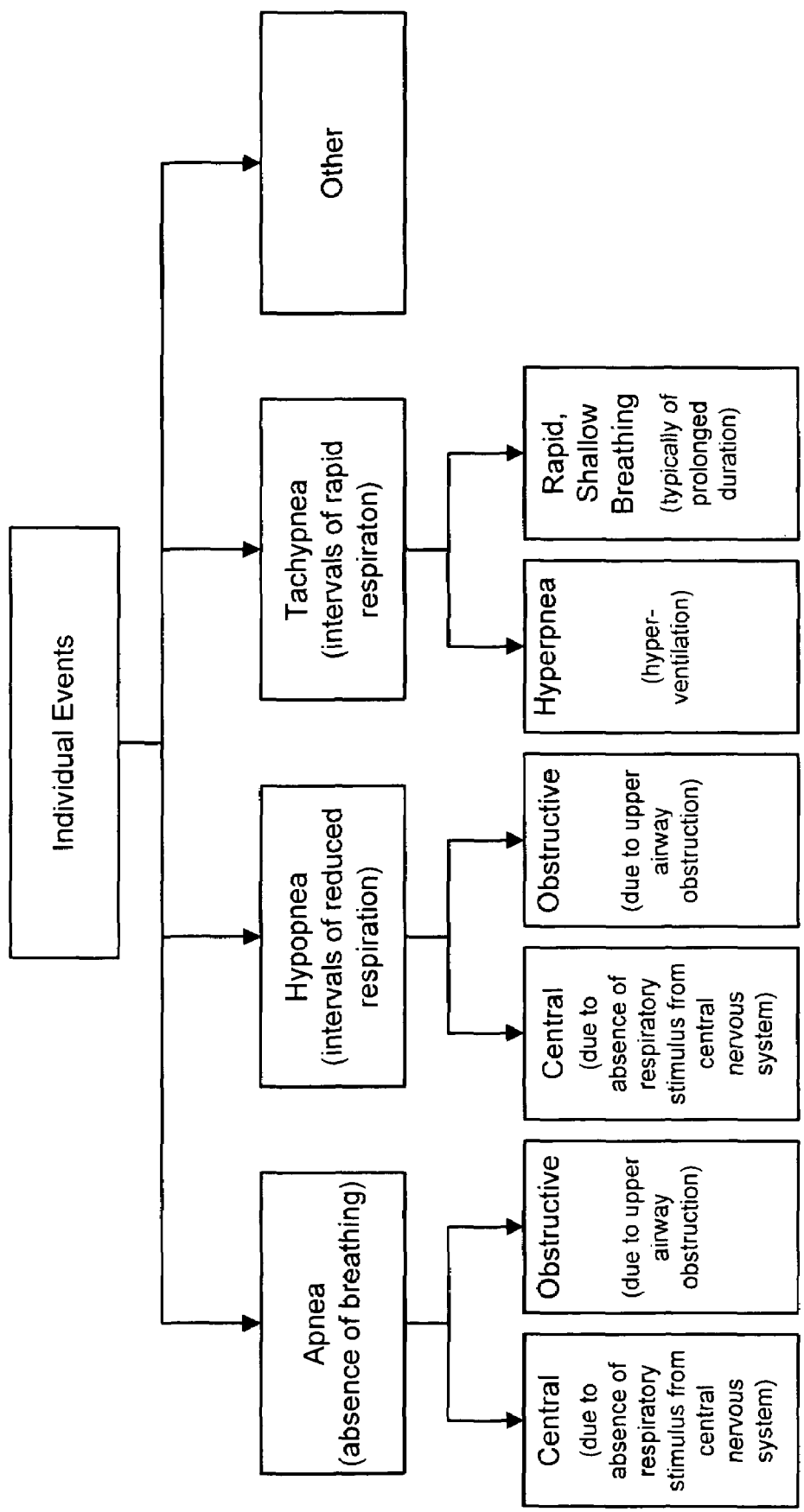
FIGS. 21A through 21G provide charts illustrating classification of individual disordered breathing events and combination of periodic breathing events that may be detected in accordance with embodiments of the invention.
Figure 21B:
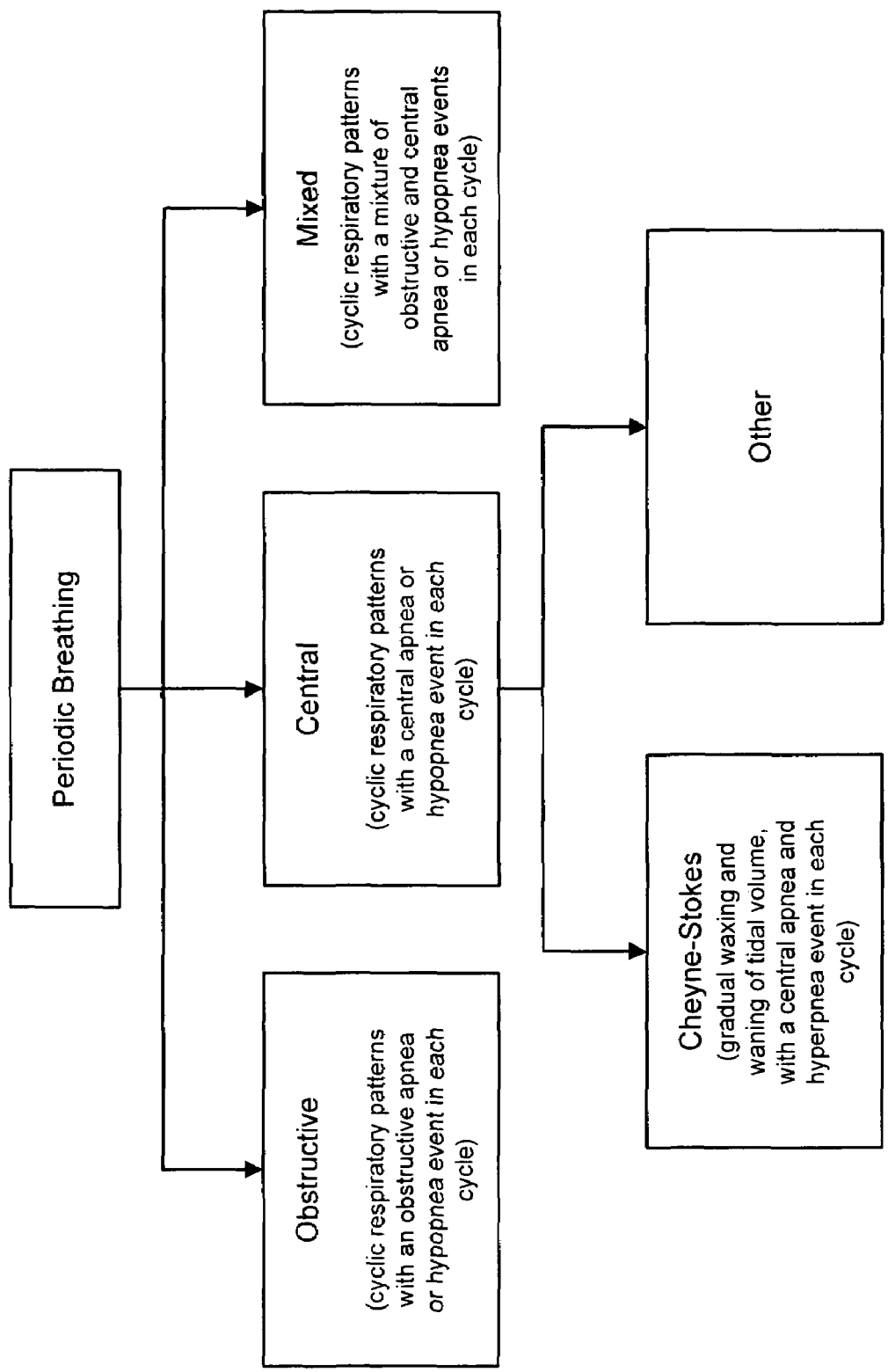
Figure 21C:
Figure 21D:
Figure 21E:
Figure 21F:
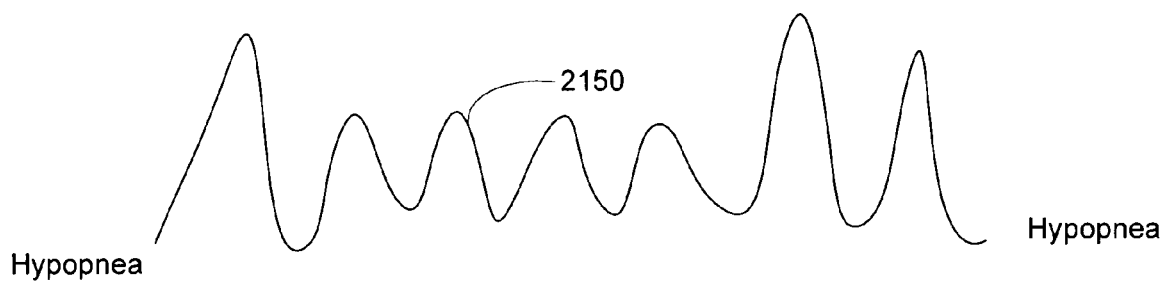

FIGS. 21A and 21B provide charts illustrating classification of individual disordered breathing events and combination of periodic breathing events, respectively. As illustrated in FIG. 21A, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 21A, apnea and hypopnea events may be further subdivided as either central events, e.g., caused either by central nervous system dysfunction, or obstructive events, e.g., caused by upper airway obstruction. A tachypnea event may be further classified as a hyperpnea event, represented by rapid deep breathing (hyperventilation). A tachypnea event may alternatively be classified as rapid shallow breathing, typically of prolonged duration.

Figure 22A:
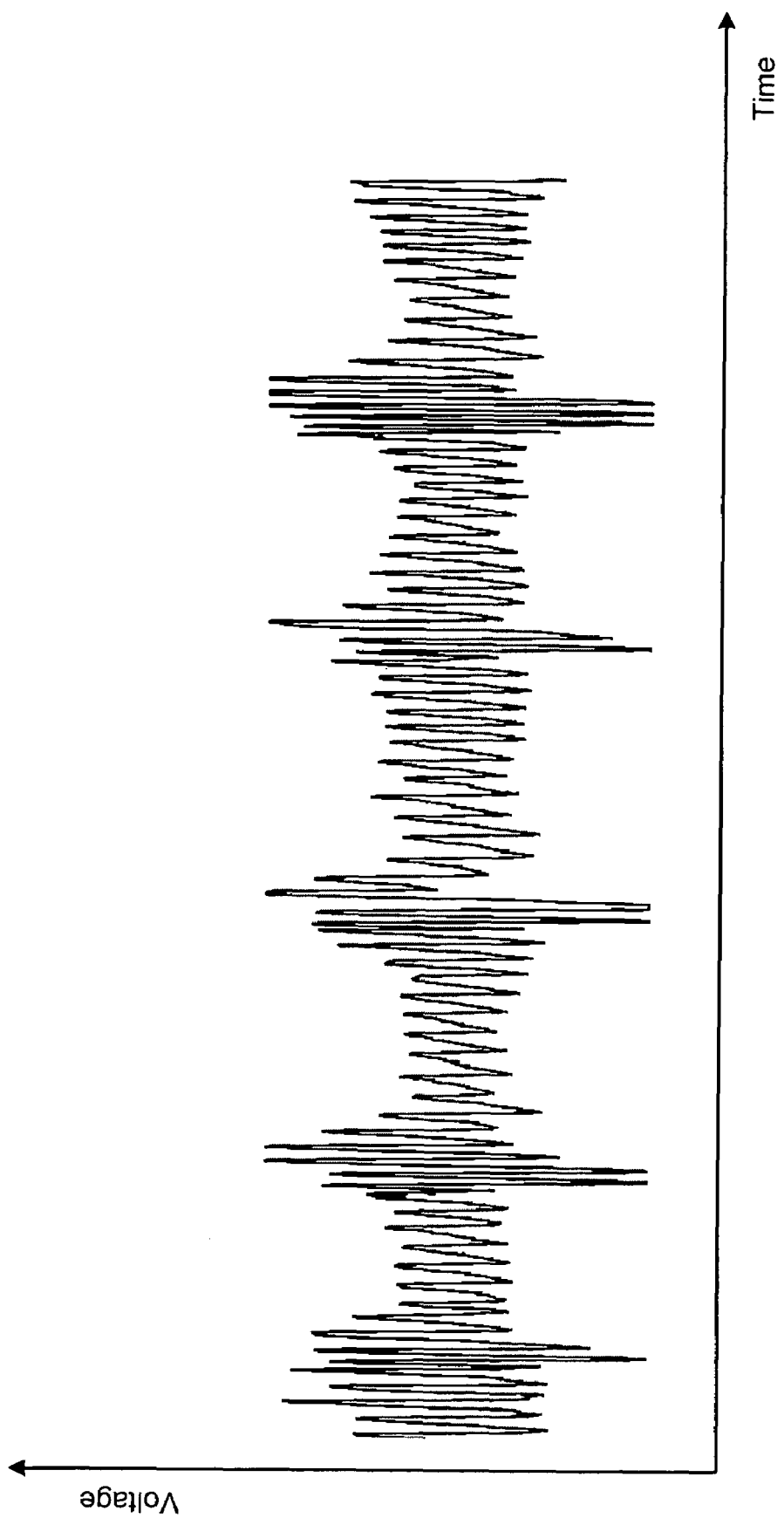
FIGS. 22A and 22B are graphs of periodic breathing and Cheyne-Stokes respiration, respectively.
Figure 22B:
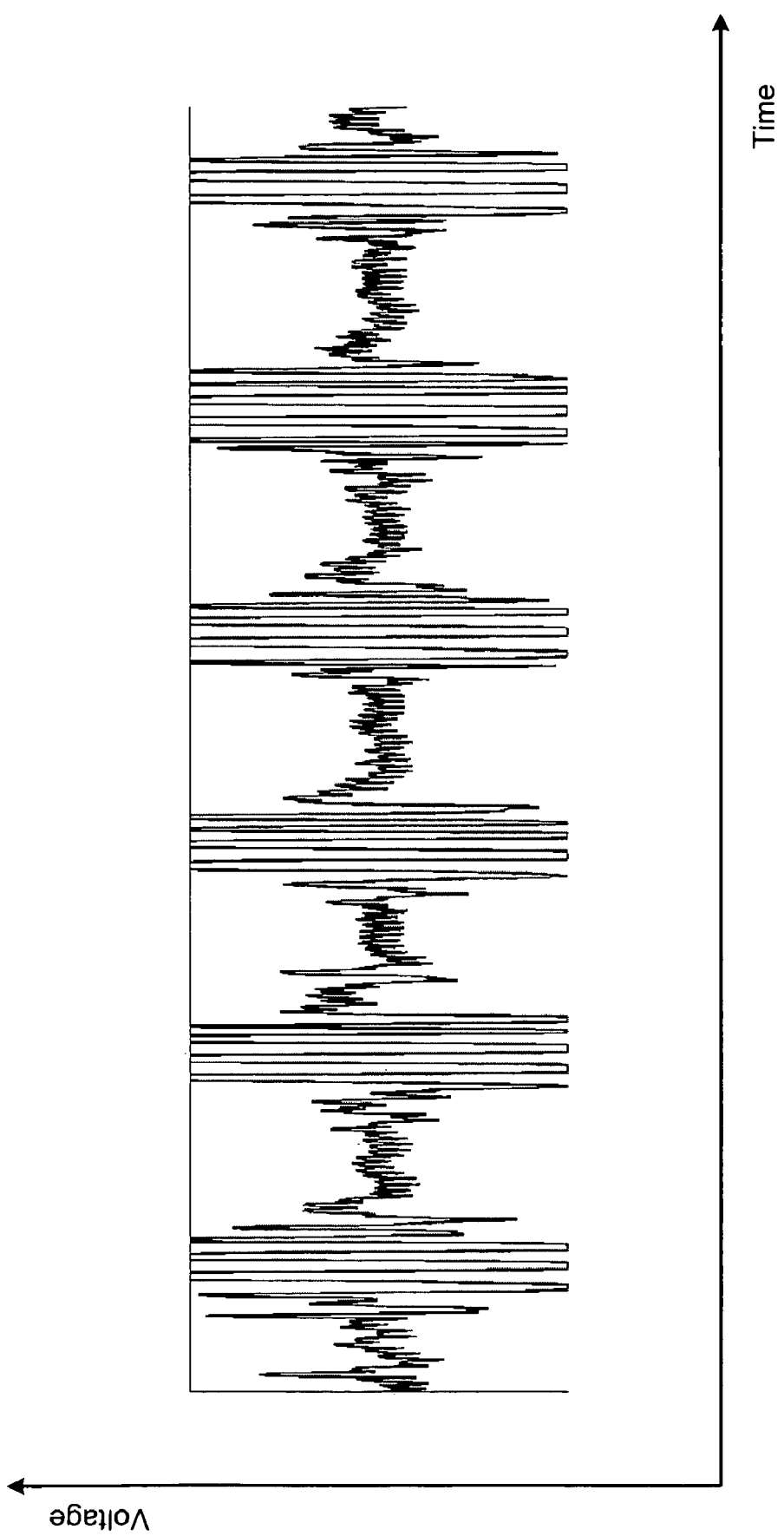

FIG. 21B illustrates classification of periodic disordered breathing events. Periodic breathing may be classified as obstructive, central or mixed. Obstructive periodic breathing is characterized by cyclic respiratory patterns with an obstructive apnea or hypopnea event in each cycle. In central periodic breathing, the cyclic respiratory patterns include a central apnea or hypopnea event in each cycle. Periodic breathing may also be of mixed origin. In this case, cyclic respiratory patterns have a mixture of obstructive and central apnea events in each cycle. A graph of respiration during periodic breathing is illustrated in FIG. 22A. Cheyne-Stokes respiration is a particular type of periodic breathing characterized by a gradual waxing and waning of tidal volume and having a central apnea and hyperpnea event in each cycle. A graph of respiration during Cheyne-Stokes respiration is illustrated in FIG. 22B. Other manifestations of periodic breathing are also possible.

Figure 21G:
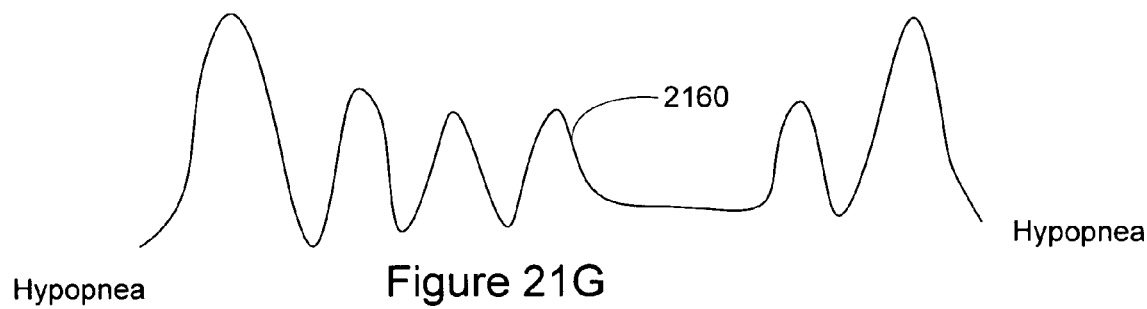

As illustrated in FIGS. 21C-G, a respiration pattern detected as a disordered breathing episode may include only an apnea respiration cycle 2110 (FIG. 21C), only hypopnea respiration cycles 2150 (FIG. 21F), or a mixture of hypopnea and apnea respiration cycles 2120 (FIG. 21D), 2130 (FIG. 21E), 2160 (FIG. 21G). A disordered breathing event 2120 may begin with an apnea respiration cycle and end with one or more hypopnea cycles. In another pattern, the disordered breathing event 2130 may begin with hypopnea cycles and end with an apnea cycle. In yet another pattern, a disordered breathing event 2160 may begin and end with hypopnea cycles with an apnea cycle in between the hypopnea cycles. Analysis of the characteristic respiration patterns associated with various types of disordered breathing may be used to detect, classify and evaluate disordered breathing episodes.

Figure 23:
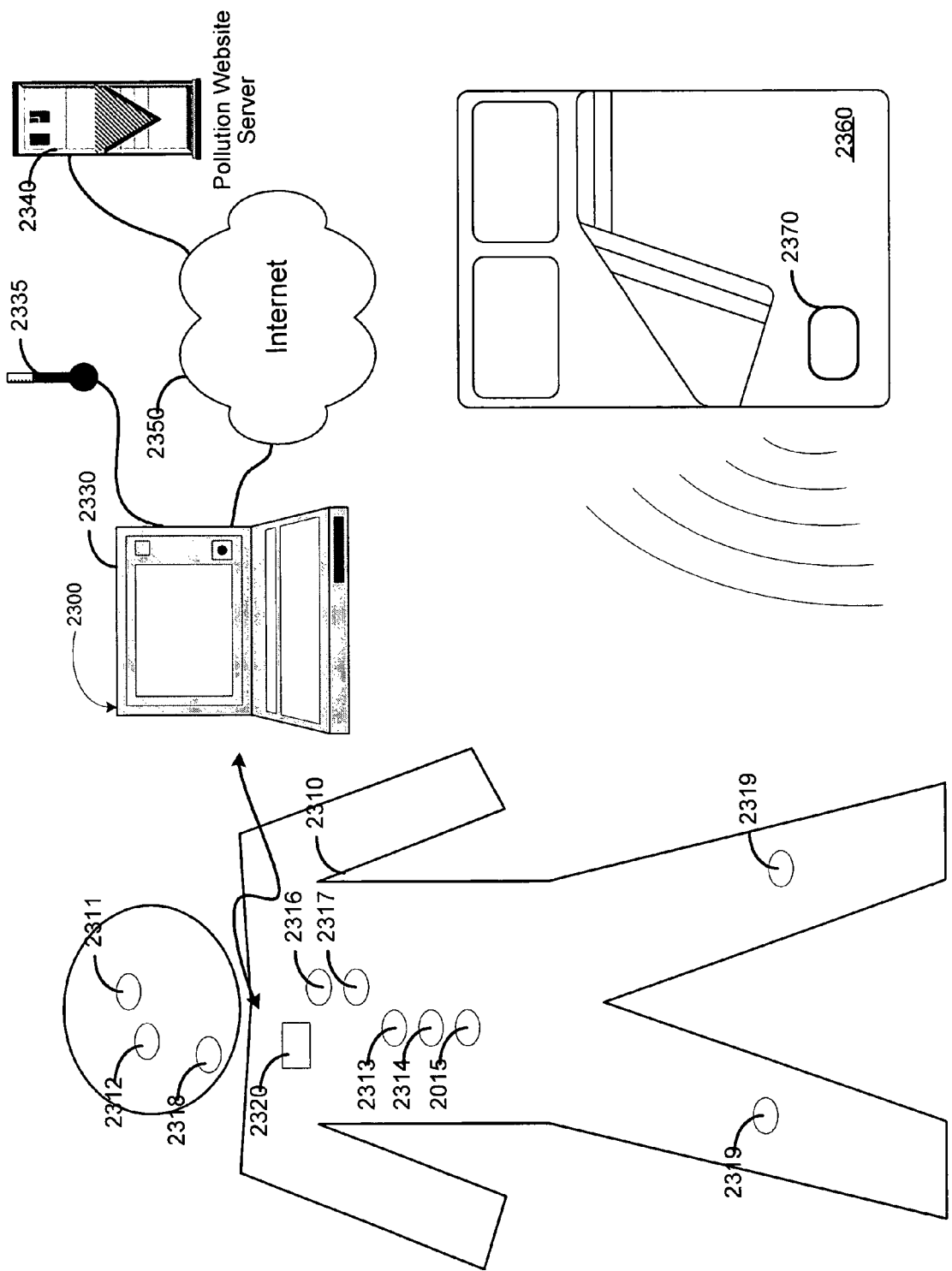
FIG. 23 illustrates a patient instrumented for acquisition of information that may be used in connection with a sleep logbook system according to embodiments of the invention.

FIG. 23 illustrates a patient 2310 instrumented for acquisition of information that may be used in connection with a sleep logbook system 2300 according to embodiments of the invention. The sleep logbook system collects sleep quality data from the patient using a number of sensors 2311-2319. In one configuration, the collected data is analyzed by a sleep quality analysis unit that may be an integrated component of an implantable medical device 2320, such as a cardiac rhythm management system. The collected data may be downloaded to a patient-external device 2330 for storage, analysis, or display. The sleep quality information may be organized as a sleep logbook entry. Elements of the sleep logbook may be displayed on a display device 2330.

In the implementation illustrated in FIG. 23, the sleep logbook system 2300 includes an implantable sleep quality data collection and analysis unit 2320 coupled to a number of sensors 2311-2319. In this example, the sensors include an EGM sensor 2316 for detecting heart rate and heart rate variability conditions. A transthoracic impedance sensor 2317 is used to detect the respiration conditions of the patient, including, for example, minute ventilation, respiration rate, and tidal volume. An activity detector, e.g., accelerometer, 2315 may be used to detect patient activity conditions. The sleep quality data system detects patient conditions including the patient's posture and location using a posture sensor 2314 and a proximity to bed sensor 2313, respectively. The sleep quality data system senses the patient's brain activity using EEG sensors 2311 and the patient's eye movements using EOG sensors 2312. Jaw and limb movements are sensed using accelerometers attached to the patient's jaw 2318 and legs 2319.

In this application, the sleep quality data collection and analysis unit 2320 is configured to track the patient's heart rate, heart rate variability, minute ventilation, respiration rate, tidal volume, posture, proximity to bed, brain activity, eye movements, jaw movements and leg movements. At periodic intervals, the system samples signals from the sensors and stores data regarding the detected conditions in memory circuitry within the sleep quality data collection and analysis unit 2320. The sleep quality data collection and analysis unit 2320 may additionally access an external input unit 2330 to detect patient reported conditions, for example, recent tobacco and medication use by the patient. Further, the sleep quality data collection and analysis unit 2320 may monitor conditions using one or more external sensors. In the illustrated example, a thermometer 2335 is coupled through the external programmer 2330 and a pollution website 2340 is accessible to the sleep quality data collection and analysis unit 2320 through the internet 2350.

The sleep quality data collection and analysis unit 2320 may operate to acquire data during periods of both sleep and wakefulness. It may be beneficial, for example, to track changes in particular conditions measured during periods of wakefulness that are associated with sleep disordered breathing. For example, some patients who suffer from sleep apnea experience changes in heart rate variability, blood pressure variability, and/or sympathetic nerve activity during periods of wakefulness. Detection and analysis of the physiological changes attributable to sleep disorders and measurable during the time the patient is awake provides a more complete picture of sleep quality.

In another example, the patient's sleep quality may be evaluated by determining the patient's activity level while the patient is awake. The activity level of the patient during the day may provide important information regarding the patient's sleep quality. For example, if the patient is very inactive during periods of wakefulness, this may indicate that the patient's sleep is of inadequate quality or duration. Such information may also be used in connection with assessing the efficacy of a particular sleep disorder therapy and/or adjusting the patient's sleep disorder therapy. Methods and systems for determining the patient's activity level and generally assessing the well-being of a patient are described in commonly owned U.S. Pat. No. 6,021,351 which is incorporated herein by reference.

The analysis unit 2320 may calculate one or more sleep quality metrics quantifying the patient's sleep quality. A representative set of the sleep quality metrics include, for example, sleep efficiency, sleep fragmentation, number of arousals per hour, denoted the arousal index (AI).

The analysis unit 2320 may also compute one or more metrics quantifying the patient's disordered breathing, such as the apnea hypopnea index (AHI) providing the number of apneas and hypopneas per hour, and the percent time in periodic breathing (% PB).

Further, metrics associated with sleep movement disorders may also be determined by the analysis unit 2320. Such metrics may include, for example, a general sleep movement disorder index (MDI) representing the number of abnormal movements arising from movement disorders such as restless leg syndrome, periodic limb movement disorder and bruxism per hour. In addition, specific indices may be calculated for each type of movement disorder, e.g., a bruxism index (BI) characterizing the number of jaw movements per hour, a RLS index (RLSI) characterizing the number of restless leg syndrome episodes per hour, and a PLM index (PLMI) characterizing the number of periodic limb movements experienced by the patient per hour.

In addition, percentage of sleep time during which the patient experiences movement disorders (% MD) may be calculated. Specific metrics relating to the percentage of time during which the patient experiences bruxism (% B), restless leg syndrome (% RLS), and periodic leg movement disorder (% PLMD) may also be determined.

Further, sleep summary metrics may be computed, either directly from the collected patient condition data, or by combining the above-listed sleep quality and sleep disorder metrics. In one embodiment, a composite sleep disordered respiration metric (SDRM) may be computed by combining the apnea hypopnea index (AHI) and the arousal index (AI). The composite sleep disordered respiration metric (SDRM) may be computed as a linear combination of the AHI and AI as follows:

$$SDRM = c_1 * AHI + c_2 * AI \quad [1]$$

where $c_1$ and $c_2$ are constants chosen to balance the relative contributions of respiratory and arousal effects on sleep disturbance. The AHI may be monitored by performing disordered breathing detection based on transthoracic impedance measurements as previously described. The AI may be estimated, for example, by monitoring the patient activity, minute ventilation, and posture sensors for body motion indicating sleep termination or arousal. A more sensitive measure of arousal may be made using EEG signals. In this implementation, the constant $c_2$ may be adjusted to reflect the increased sensitivity to arousal.

In another embodiment, an undisturbed respiration sleep time (URST) or undisturbed respiration sleep efficiency (URSE) may be computed based on the amount of time the patient spends asleep in bed without respiratory disturbance.

The URST or URSE metrics may be determined using three parameters: total time in bed (TIB), total time asleep (TA), and combined sleep time duration in disturbed respiration (STDR). Time in bed may be determined by a combination of posture sensing and sensing the proximity of the patient to bed. The posture condition of the patient may determined, for example, using an implantable multiaxis accelerometer sensor.

The patient's total time in bed (TIB) may be determined using a proximity to bed sensor. The proximity to bed sensor may use a receiver in the sleep quality data collection and analysis unit 2320 for receiving signals transmitted from a beacon 2370 located at the patient's bed 2360. If the proximity to bed receiver detects a signal of sufficient strength from the proximity to bed beacon 2370, then the receiver detects that the patient is in bed 2360.

Total time asleep (TA) may be determined using the sleep detection method described in more detail above. The total sleep time in disturbed respiration (STDR) may be determined, for example, based on detection of sleep and disordered breathing using the sleep and disordered breathing detection methods described above.

The patient's undisturbed respiration sleep time (URST) is calculated as:

$$URST = TA - STDR \quad [2]$$

where TA=total time asleep and STDR=sleep time in disturbed breathing.

The undisturbed respiration sleep efficiency (URSE) in percent is calculated $$URSE = 100 * URST/TIB \quad [3]$$

where URST=undisturbed respiration sleep time and TIB=total time in bed.

Similar metrics may be calculated for movement disorders generally, or for specific movement disorders, e.g., RLS, PLMD, or bruxism. For example, the composite RLS, PLMD, and bruxism metrics, RLSM, PLMDM, and BM, respectively, may be calculated using equations similar in form to equation 1 above:

$$RLSM = c_1 * RLSI + c_2 * AI \quad [4]$$

where RLSI=number of restless leg movement syndrome episodes per hour, AI=number of arousals per hour, and $c_1$ and $c_2$ are constants chosen to balance the relative contributions of abnormal movement and arousal effects on sleep disturbance.

$$PLMDM = c_1 * PLMDI + c_2 * AI \quad [5]$$

where PLMDI=number of periodic leg movement syndrome episodes per hour, AI=number of arousals per hour, and $c_1$ and $c_2$ are constants chosen to balance the relative contributions of abnormal movement and arousal effects on sleep disturbance.

$$BM = c_1 * BMI + c_2 * AI \quad [6]$$

where BMI=number of bruxism movement episodes per hour, AI=number of arousals per hour, and $c_{1\ and\ c2}$ are constants chosen to balance the relative contributions of abnormal movement and arousal effects on sleep disturbance.

The patient's undisturbed movement sleep time (UMST) and undisturbed movement sleep efficiency (UMSE) may be calculated for each movement related disorder separately or in combination using equations similar in form to equations 2 and 3, above.

In addition, a composite sleep disorder index SDI quantifying the combined effect of both respiratory and movement disorders may be computed by combining the apnea hypopnea index (AHI), the movement disorder index (MDI), and the arousal index (AI).

A sleep disturbance index (SDI) may be computed as a linear combination of the AHI, and the combined disorder index $DI_C$. The combined disorder index may include both abnormal breathing and movement components. For example, the sleep disturbance index SDI is characterizable by the equation:

$$SDI = c_4 * DI_C + c_3 * AI, \quad [7]$$

where $DI_C$ is a combined disorder index of the form:

$$DI_C = c_{41} * DI_1 + c_{42} * DI_2 \quad [7a]$$

In equation 7, $c_4$ and $c_3$ are constants chosen to balance the relative contributions of the combined disorder and arousal effects, respectively. The disorder index, $DI_C$, may be used to characterize the effects of one or more sleep disorders, including, e.g., disorders associated with disturbed respiration and/or abnormal movements. The combined disorder index may represent only one disorder index, or may be a linear combination of two or more sleep disorder indices, e.g., the apnea/hypopnea index (AHI) and the abnormal movement disorder index (MDI). The constants $c_{41}$ and $c_{42}$ may be used as weighting factors associated with particular disorder indices.

The patient's undisturbed sleep time (UST) may be calculated:

$$UST = TA - STSD \quad [8]$$

where TA=total time asleep and STSD=sleep time spent in sleep disorders.

The undisturbed sleep efficiency (USE) in percent may be calculated:

$$USE = 100 * UST / TIB \quad [9]$$

where UST=undisturbed sleep time and TIB=total time in bed.

Sleep quality metrics, such as those described above, or other metrics, may be acquired and analyzed using the sleep quality data collection and analysis unit 2320. Sleep quality metrics, in addition to raw or processed data based on physiological and non-physiological conditions may determined periodically, e.g., daily, and stored or transmitted to another device. Such data can be presented to the patient's health care professional on a real-time basis, or as a long-term, e.g., month long or year long, trend of daily measurements.

The health care professional may access the data during clinic visits via programmer interrogation of the implanted device, through occasional or periodic trans-telephonic device interrogations, or through an automatic or "on-demand" basis in the context of an advanced patient management system. The health care professionals may use the sleep quality indicator trends alone or in conjunction with other device-gathered or clinical data to diagnose disorders and/or adjust the patient's device or medical therapy as needed to improve the patient's quality of sleep.

Figure 25:
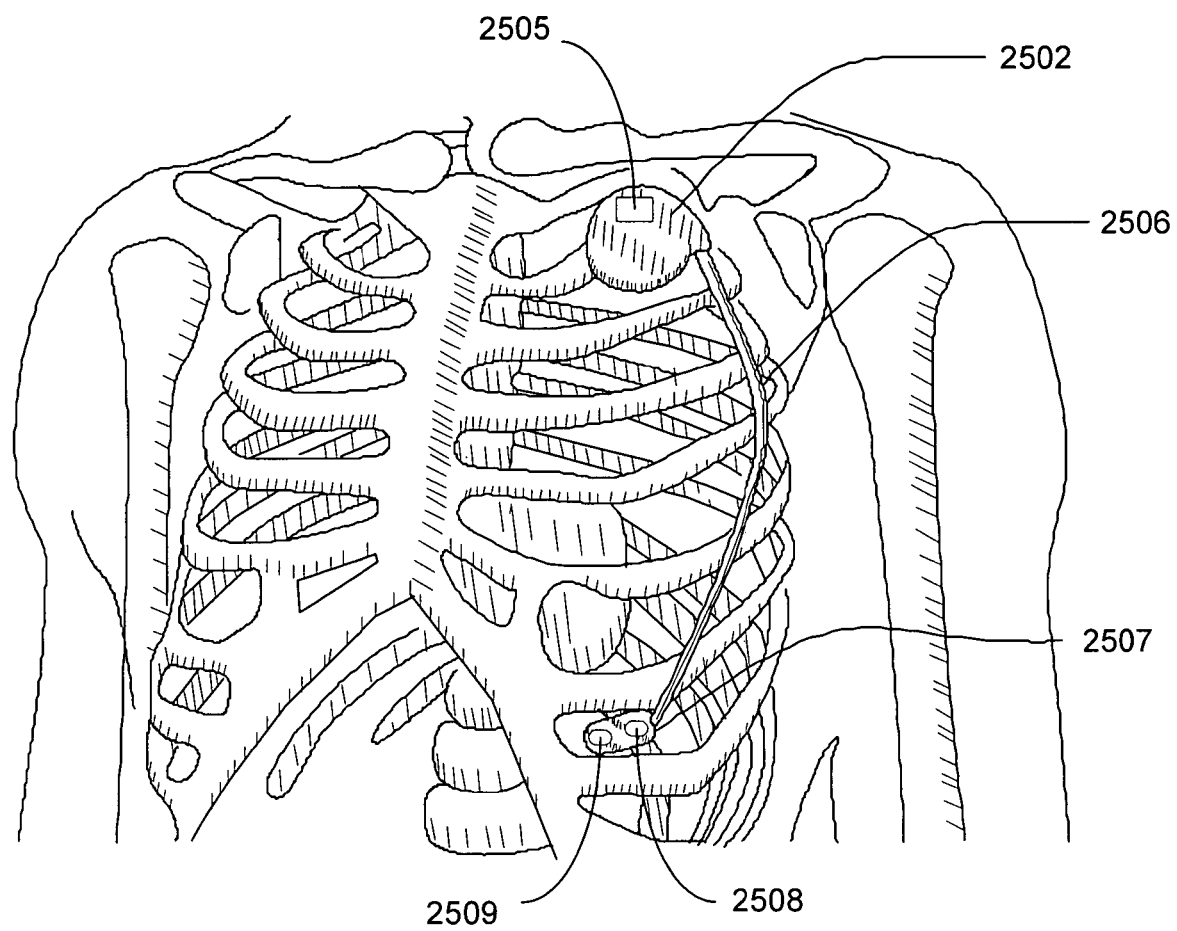
FIG. 25 is a diagram illustrating an implantable transthoracic cardiac device that may be used in connection with acquiring and organizing data for a sleep logbook in accordance with embodiments of the invention.

FIG. 25 is a partial view of an implantable device that may include circuitry for implementing a sleep logbook circuitry 2435 in accordance with embodiments of the invention. In this example, the implantable device comprises a cardiac rhythm management device (CRM) 2400 including an implantable pulse generator 2405 electrically and physically coupled to an intracardiac lead system 2410. The respiratory logbook system may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 2410 are inserted into the patient's heart 2490. The intracardiac lead system 2410 includes one or more electrodes configured to sense electrical cardiac activity of the heart, deliver electrical stimulation to the heart, sense the patient's transthoracic impedance, and/or sense other physiological parameters, e.g, cardiac chamber pressure or temperature. Portions of the housing 2401 of the pulse generator 2405 may optionally serve as a can electrode.

Communications circuitry is disposed within the housing 2401 for facilitating communication between the pulse generator 2405 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 2405 may optionally incorporate a motion detector 2420 that may be used to sense various respiration-related conditions. For example, the motion detector 2420 may be optionally configured to sense snoring, activity level, and/or chest wall movements associated with respiratory effort, for example. The motion detector 2420 may be implemented as an accelerometer positioned in or on the housing 2401 of the pulse generator 2405. If the motion sensor is implemented as an accelerometer, the motion sensor may also provide respiratory, e.g. rales, coughing, and cardiac, e.g. S1-S4 heart sounds, murmurs, and other acoustic information.

The lead system 2410 of the CRM 2400 may incorporate one or more transthoracic impedance sensors that may be used to acquire the patient's respiration waveform, or other respiration-related information. The transthoracic impedance sensor may include, for example, one or more intracardiac electrodes 2441, 2442, 2451-2455, 2463 positioned in one or more chambers of the heart 590. The intracardiac electrodes 2441, 2442, 2451-2455, 2463 may be coupled to impedance drive/sense circuitry 2430 positioned within the housing of the pulse generator 2405.

In one implementation, impedance drive/sense circuitry 2430 generates a current that flows through the tissue between an impedance drive electrode 2451 and a can electrode on the housing 2401 of the pulse generator 2405. The voltage at an impedance sense electrode 2452 relative to the can electrode changes as the patient's transthoracic impedance changes. The voltage signal developed between the impedance sense electrode 2452 and the can electrode is detected by the impedance sense circuitry 2430. Other locations and/or combinations of impedance sense and drive electrodes are also possible.

The voltage signal developed at the impedance sense electrode 2452, illustrated in FIG. 14, is proportional to the patient's transthoracic impedance and represents the patient's respiration waveform. The transthoracic impedance increases during respiratory inspiration 1410 and decreases during respiratory expiration 1420. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions, as indicated in FIG. 14.

Figure 24:
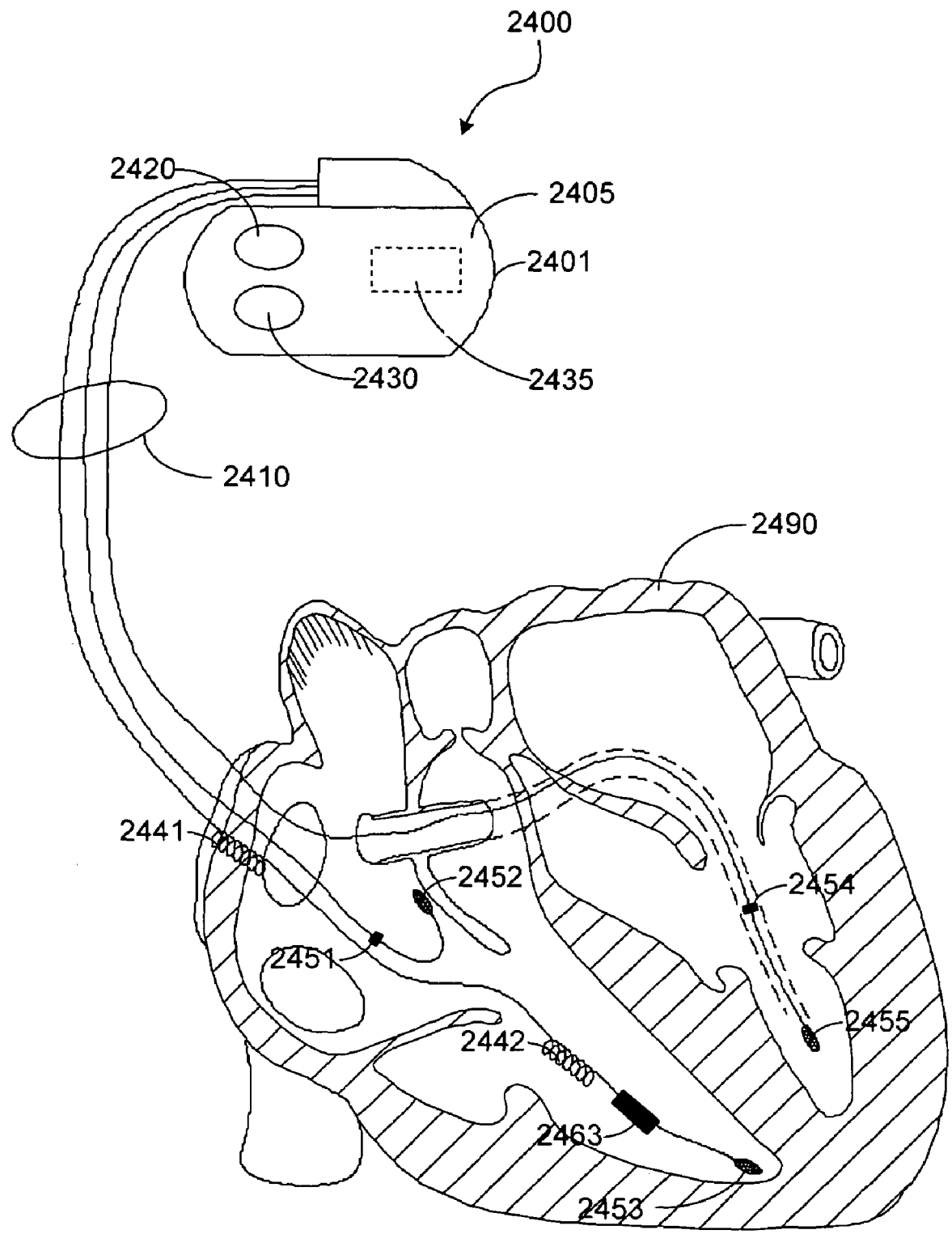
FIG. 24 is a partial view of an implantable device that may include a sleep logbook system in accordance with embodiments of the invention.

Returning to FIG. 24, the lead system 2410 may include one or more cardiac pace/sense electrodes 2451-2455 positioned in, on, or about one or more heart chambers for sensing electrical signals from the patient's heart 2490 and/or delivering pacing pulses to the heart 2490. The intracardiac sense/pace electrodes 2451-2455, such as those illustrated in FIG. 24, may be used to sense and/or pace one or more chambers of the heart, including the left ventricle, the right ventricle, the left atrium and/or the right atrium. The lead system 2410 may include one or more defibrillation electrodes 2441, 2442 for delivering defibrillation/cardioversion shocks to the heart.

The pulse generator 2405 may include circuitry for detecting cardiac arrhythmias and/or for controlling pacing or defibrillation therapy in the form of electrical stimulation pulses or shocks delivered to the heart through the lead system 2410. Circuitry for implementing a sleep logbook 2435, may be housed within the pulse generator 2405. The sleep logbook circuitry 2435 may be coupled to various sensors, patient input devices, and/or information systems through leads or through wireless communication links.

FIG. 25 is a diagram illustrating an implantable transthoracic cardiac device that may be used in connection with acquiring and organizing data for a sleep logbook in accordance with embodiments of the invention. The implantable device illustrated in FIG. 25 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a sleep logbook system may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches.

In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 25, a subcutaneous electrode assembly 2507 can be positioned under the skin in the chest region and situated distal from the housing 2502. The subcutaneous and, if applicable, housing electrode(s) can be positioned about the heart at various locations and orientations, such as at various anterior and/or posterior locations relative to the heart. The subcutaneous electrode assembly 2507 is coupled to circuitry within the housing 2502 via a lead assembly 2506. One or more conductors (e.g., coils or cables) are provided within the lead assembly 2506 and electrically couple the subcutaneous electrode assembly 2507 with circuitry in the housing 2502. One or more sense, sense/pace or defibrillation electrodes can be situated on the elongated structure of the electrode support, the housing 2502, and/or the distal electrode assembly (shown as subcutaneous electrode assembly 2507 in the configuration shown in FIG. 25).

It is noted that the electrode and the lead assemblies 2507, 2506 can be configured to assume a variety of shapes. For example, the lead assembly 2506 can have a wedge, chevron, flattened oval, or a ribbon shape, and the subcutaneous electrode assembly 2507 can comprise a number of spaced electrodes, such as an array or band of electrodes. Moreover, two or more subcutaneous electrode assemblies 2507 can be mounted to multiple electrode support assemblies 2506 to achieve a desired spaced relationship amongst subcutaneous electrode assemblies 2507.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent applications Ser. No. 60/462,272, filed Apr. 11, 2003, Ser. No. 10/462,001, filed Jun. 13, 2003, now U.S. Publication No. 2004/0230229, Ser. No. 10/465,520, filed Jun. 19, 2003, now U.S. Publication No. 2004/0230230, Ser. No. 10/820,642, filed Apr. 8, 2004, now U.S. Publication No. 2004/0215258, all of which are incorporated herein by reference.

The housing of the ITCS device may incorporate components of a sleep logbook system 2505, including a memory, interface, event processor and/or event detector circuitry. The sleep logbook circuitry may be coupled to one or more sensors, patient input devices, and/or information systems as described in connection with FIG. 2.

In one implementation, the ITCS device may include an impedance sensor configured to sense the patient's transthoracic impedance. The transthoracic impedance sensor may include impedance drive/sense circuitry within the housing 2502 coupled to a can electrode and to one or more impedance electrodes 2508, 2509 positioned on the subcutaneous electrode assembly 2507. The impedance drive circuitry generates a current that flows between a subcutaneous impedance drive electrode 2509 and the can electrode on the primary housing 2502 of the ITCS device. The voltage at a subcutaneous impedance sense electrode 2508 relative to the can electrode changes as the patient's transthoracic impedance changes. The voltage signal developed between the impedance sense electrode 2508 and the can electrode is sensed by the impedance sense circuitry, producing a signal such as that depicted in FIG. 14.

Communications circuitry is disposed within the housing 2502 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

The present invention provides diagnostic, monitoring, and evaluation capabilities relating to sleep quality and may be particularly valuable in the context of an advanced patient management system. Undiagnosed sleep disorders can lead to increased morbidity and mortality, such as those arising from various respiratory and cardiovascular consequences. Routine monitoring of patient sleep quality may lead to improved diagnosis and treatment of these syndromes and their associated co-morbidities. The invention may provide less obtrusive sleep quality monitoring, particularly and is suited for patients having an implanted device. The present invention serves to improve diagnosis of sleep disorders by reducing the inconveniences, unnatural sleep environment issues, and expenses associated with sleep clinic polysomnogram studies.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An automated method for collecting and organizing information associated with sleep of a patient, comprising:
   detecting sleep;
   acquiring information associated with sleep, the information including a sleep-related event and one or more sensed physiological conditions of the patient associated with the sleep-related event; and
   organizing the acquired information as an entry in a sleep logbook that maintains the association between the one or more sensed physiological conditions and the sleep-related event, the entry being one of a plurality of such entries in the sleep logbook for a corresponding plurality of sleep-related events;
   wherein at least one of detecting, acquiring, and organizing is performed at least in part implantably.

2. The method of claim 1, wherein acquiring the information associated with sleep comprises controlling acquisition of the information based on a triggering event.

3. The method of claim 1, wherein the sleep-related event comprises a sleep disorder event occurring during sleep, and wherein acquiring the information associated with sleep comprises detecting the sleep disorder event.

4. The method of claim 3, wherein detecting the sleep disorder event comprises detecting one or more disordered breathing events.

5. The method of claim 3, wherein detecting the sleep disorder event comprises detecting one or more movement disorder events.

6. The method of claim 1, wherein acquiring the information associated with sleep comprises acquiring information related to sleep quality.

7. The method of claim 1, further comprising:
   receiving an instruction that programmably controls the type of the information that is acquired in the acquiring step and organized in the organizing step.

8. The method of claim 1, wherein acquiring the information associated with sleep comprises:
   detecting or predicting the sleep-related event; and
   acquiring information regarding the one or more sensed physiological conditions responsive to the detection or prediction of the event.

9. The method of claim 8, wherein acquiring information responsive to the detection or prediction of the event comprises acquiring information proximate in time to the detected sleep-related event.

10. The method of claim 1, further comprising assessing sleep quality using the acquired information.

11. The method of claim 1, wherein organizing the information as the sleep logbook comprises organizing the plurality of entries in the sleep logbook into groups according to type of sleep-related event.

12. The method of claim 1, wherein the organizing the information as the sleep logbook comprises organizing the plurality of entries chronologically.

13. The method of claim 1, further comprising storing the organized information in an implantable device.

14. The method of claim 1, further comprising providing a user interface for accessing the sleep logbook.

15. The method of claim 14, wherein providing the user interface comprises providing an interactive input/output device.

16. The method of claim 14, wherein providing the user interface comprises generating a menu of sleep logbook events.

17. The method of claim 14, wherein providing the user interface comprises displaying the organized information.

18. A sleep logbook system, comprising:
   a sleep detector configured to detect sleep;
   a data acquisition unit configured to acquire information related to sleep, the information including a sleep-related event and one or more sensed physiological conditions of the patient associated with the sleep-related event; and
   a processor, coupled to the sleep detector and the data acquisition unit, the processor configured to organize the acquired information as an entry in a sleep logbook that maintains the association between the one or more sensed physiological conditions and the sleep-related event, the entry being one of a plurality of such entries in the sleep logbook for a corresponding plurality of sleep-related events;
   wherein at least one of the sleep detector, the data acquisition unit, and the processor is implantable or comprises an implantable component.

19. The system of claim 18, wherein the data acquisition unit is responsive to an instruction that programmably controls the type of information that is acquired by the data acquisition unit.

20. The system of claim 18, wherein the information that the data acquisition unit is configured to acquire includes non-physiological information.

21. The system of claim 18, wherein the sleep-related event comprises a sleep disorder event occurring during sleep, and wherein the data acquisition unit is configured to detect the sleep disorder event.

22. The system of claim 18, wherein the information that the data acquisition unit is configured to acquire includes information related to sleep quality.

23. The system of claim 18, wherein the data acquisition unit is configured to detect or predict the sleep-related event and to acquire the information responsive to the detection or prediction of the sleep-related event.

24. The system of claim 23, wherein the data acquisition unit is configured to acquire information proximate in time to the detected or predicted sleep-related event.

25. The system of claim 18, wherein the processor is configured to determine one or more metrics associated with sleep.

26. The system of claim 18, wherein the processor is configured to organize the plurality of entries in the sleep logbook into groups according to type of sleep-related event.

27. The system of claim 18, further comprising a memory coupled to the processor and configured to store the organized sleep information.

28. The system of claim 18, further comprising a display unit coupled to the processor and configured to display the organized sleep information.

29. The system of claim 28, further comprising a user interface, coupled to the processor, and configured to provide user access to the sleep logbook.

30. The system of claim 29, wherein the user interface is configured to provide access to data associated with therapy.

31. The system of claim 29, wherein the user interface is configured to provide access to diagnostic information.

32. The system of claim 29, wherein the user interface comprises an interactive input/output device.

33. The system of claim 29, wherein the user interface is configured to generate a menu of sleep logbook entries.

34. The system of claim 33, wherein the user interface further comprises an input mechanism, the input mechanism configured to select one or more of the plurality of entries in the sleep logbook from the menu.

35. The system of claim 29, wherein the user interface is configured to access summary information associated with the acquired information.

36. An automated system for collecting and organizing information associated with sleep, comprising:

means for detecting sleep;

means for acquiring information associated with sleep, the information including a sleep-related event and one or more sensed physiological conditions of the patient associated with the sleep-related event; and means for organizing the information as an entry of a sleep logbook that maintains the association between the one or more sensed physiological conditions and the sleep-related event, the entry being one of a plurality of such entries in the sleep logbook for a corresponding plurality of sleep-related events;

wherein at least one of the means for detecting, the means for acquiring, and the means for organizing comprises an implantable component.

37. The system of claim 36, wherein the sleep-related event comprises a sleep disorder event occurring during sleep, the system further comprising means for detecting the sleep disorder event.

38. The system of claim 36, wherein the sleep-related event comprises a sleep disorder event occurring during sleep, the system further comprising:

means for detecting or predicting the sleep disorder event; and means for controlling acquisition of information responsive to the detection or prediction of the sleep disorder event.

39. The system of claim 36, wherein the organizing means organizes the plurality of entries in the sleep logbook into groups according to type of sleep-related event.

40. The system of claim 36, wherein the acquiring means is responsive to an instruction that programmably controls the type of information that is acquired.

* * * * *

UNITED STATES PATENT AND TRADEMARK OFFICE
CERTIFICATE OF CORRECTION

PATENT NO. : 7,572,225 B2
APPLICATION NO. : 10/920569
DATED : August 11, 2009
INVENTOR(S) : Stahmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1293 days.

Signed and Sealed this

Fourteenth Day of December, 2010

David J. Kappos
*Director of the United States Patent and Trademark Office*